US011678906B2

(12) United States Patent
Choi et al.

(10) Patent No.: US 11,678,906 B2
(45) Date of Patent: Jun. 20, 2023

(54) MULTI-PORTAL SURGICAL SYSTEMS, CANNULAS, AND RELATED TECHNOLOGIES

(71) Applicant: Amplify Surgical, Inc., Laguna Hills, CA (US)

(72) Inventors: Andy Wonyong Choi, Irvine, CA (US); Dong-Hwa Heo, Seoul (KR); Jeffrey Roh, Seattle, WA (US)

(73) Assignee: Amplify Surgical, Inc., Irvine, CA (US)

( * ) Notice: Subject to any disclaimer, the term of this patent is extended or adjusted under 35 U.S.C. 154(b) by 408 days.

(21) Appl. No.: 16/687,520

(22) Filed: Nov. 18, 2019

(65) Prior Publication Data

US 2021/0068863 A1    Mar. 11, 2021

Related U.S. Application Data

(63) Continuation-in-part of application No. 16/565,403, filed on Sep. 9, 2019.

(51) Int. Cl.
*A61B 17/34* (2006.01)
*A61B 5/00* (2006.01)
(Continued)

(52) U.S. Cl.
CPC ............ *A61B 17/3423* (2013.01); *A61B 5/24* (2021.01); *A61B 5/4893* (2013.01);
(Continued)

(58) Field of Classification Search
CPC ....................................... A61B 17/3421–3423
See application file for complete search history.

(56) References Cited

U.S. PATENT DOCUMENTS 5,390,683 A    2/1995  Pisharodi
5,437,637 A *  8/1995  Lieber ................. A61M 25/003
                                                600/549
(Continued)

FOREIGN PATENT DOCUMENTS

CN      105636555 A    6/2016
EP        3016617 A2   5/2016
(Continued)

OTHER PUBLICATIONS

Choi, Chang Myong et al. "How I do it? Biportal endoscopic spinal surgery (BESS) for treatment of lumbar spinal stenosis." Acta Neurochir (2016) 158:459-463; published Jan. 18, 2016.
(Continued)

*Primary Examiner* — Eduardo C Robert
*Assistant Examiner* — Steven J Cotroneo
(74) *Attorney, Agent, or Firm* — Perkins Coie LLP

(57) ABSTRACT

A multi-portal method for treating a subject's spine includes distracting adjacent vertebrae using a distraction instrument positioned at a first entrance along the subject to enlarge an intervertebral space between the adjacent vertebrae. An interbody fusion implant can be delivered into the enlarged intervertebral space. The interbody fusion implant can be positioned directly between vertebral bodies of the adjacent vertebrae while endoscopically viewing the interbody fusion implant using an endoscopic instrument. The patient's spine can be visualized using endoscopic techniques to view, for example, the spine, tissue, instruments, and implants before, during, and after implantation, or the like. The visualization can help a physician throughout the surgical procedure to improve patient outcome.

17 Claims, 20 Drawing Sheets

(51) Int. Cl.
  *A61B 5/24*    (2021.01)
  *A61N 7/00*    (2006.01)
  *A61B 90/00*   (2016.01)
  *A61B 17/00*   (2006.01)
  *A61B 8/08*    (2006.01)
  *A61N 1/36*    (2006.01)
  *A61N 5/06*    (2006.01)

(52) U.S. Cl.
  CPC ............ *A61B 5/6852* (2013.01); *A61B 8/085* (2013.01); *A61B 2017/003* (2013.01); *A61B 2017/0042* (2013.01); *A61B 2017/00199* (2013.01); *A61B 2017/00261* (2013.01); *A61B 2017/00367* (2013.01); *A61B 2017/00398* (2013.01); *A61B 2017/00544* (2013.01); *A61B 2017/00973* (2013.01); *A61B 2017/3445* (2013.01); *A61B 2090/376* (2016.02); *A61B 2217/005* (2013.01); *A61B 2217/007* (2013.01); *A61B 2505/05* (2013.01); *A61B 2562/0209* (2013.01); *A61B 2562/04* (2013.01); *A61N 1/36017* (2013.01); *A61N 2005/0612* (2013.01); *A61N 2007/0047* (2013.01)

(56) References Cited

U.S. PATENT DOCUMENTS

| | | | |
|---|---|---|---|
| 5,690,222 A * | 11/1997 | Peters | B65D 75/326 |
| | | | 206/592 |
| 5,762,629 A * | 6/1998 | Kambin | A61B 17/3421 |
| | | | 604/524 |
| 5,782,832 A | 7/1998 | Larsen et al. | |
| 5,846,182 A * | 12/1998 | Wolcott | A61B 1/00135 |
| | | | 128/207.14 |
| 6,126,689 A | 10/2000 | Brett | |
| 6,162,170 A * | 12/2000 | Foley | A61M 29/00 |
| | | | 600/184 |
| 6,348,058 B1 * | 2/2002 | Melkent | A61B 17/1757 |
| | | | 606/97 |
| 6,409,766 B1 | 6/2002 | Brett | |
| 6,641,614 B1 | 11/2003 | Wagner et al. | |
| 6,723,126 B1 | 4/2004 | Berry | |
| 6,969,392 B2 | 11/2005 | Gitis et al. | |
| 7,083,650 B2 | 8/2006 | Moskowitz et al. | |
| 7,087,055 B2 | 8/2006 | Lim et al. | |
| 7,731,751 B2 | 6/2010 | Butler et al. | |
| 7,922,729 B2 | 4/2011 | Michelson | |
| RE42,525 E * | 7/2011 | Simonson | A61B 17/0218 |
| | | | 604/117 |
| 8,016,767 B2 * | 9/2011 | Miles | A61B 1/06 |
| | | | 600/245 |
| 8,062,375 B2 | 11/2011 | Glerum et al. | |
| 8,353,963 B2 | 1/2013 | Glerum | |
| 8,382,842 B2 | 2/2013 | Greenhalgh et al. | |
| 8,394,145 B2 | 3/2013 | Weiman | |
| 8,398,713 B2 | 3/2013 | Weiman | |
| 8,425,613 B2 | 4/2013 | Theofilos | |
| 8,435,298 B2 | 5/2013 | Weiman | |
| 8,491,659 B2 | 7/2013 | Weiman | |
| 8,512,407 B2 | 8/2013 | Butler et al. | |
| 8,518,120 B2 | 8/2013 | Glerum et al. | |
| 8,556,979 B2 | 10/2013 | Weiman et al. | |
| 8,568,317 B1 * | 10/2013 | Gharib | A61B 8/085 |
| | | | 600/437 |
| 8,632,594 B2 | 1/2014 | Williams et al. | |
| 8,632,595 B2 | 1/2014 | Weiman | |
| 8,679,183 B2 | 3/2014 | Glerum et al. | |
| 8,685,098 B2 | 4/2014 | Glerum et al. | |
| 8,709,086 B2 | 4/2014 | Glerum | |
| 8,845,731 B2 | 9/2014 | Weiman | |
| 8,845,732 B2 | 9/2014 | Weiman | |
| 8,845,734 B2 | 9/2014 | Weiman | |
| 8,852,279 B2 | 10/2014 | Weiman | |
| 8,864,833 B2 | 10/2014 | Glerum et al. | |
| 8,888,853 B2 | 11/2014 | Glerum et al. | |
| 8,888,854 B2 | 11/2014 | Glerum et al. | |
| 8,926,704 B2 | 1/2015 | Glerum et al. | |
| 8,940,048 B2 | 1/2015 | Butler et al. | |
| 8,986,386 B2 | 3/2015 | Oglaza et al. | |
| 9,034,041 B2 | 5/2015 | Wolters et al. | |
| 9,039,771 B2 | 5/2015 | Glerum et al. | |
| 9,044,342 B2 | 6/2015 | Perloff et al. | |
| 9,078,769 B2 | 7/2015 | Farin | |
| 9,119,730 B2 | 9/2015 | Glerum et al. | |
| 9,125,757 B2 | 9/2015 | Weiman | |
| 9,149,367 B2 | 10/2015 | Davenport et al. | |
| 9,155,628 B2 | 10/2015 | Glerum et al. | |
| 9,186,258 B2 | 11/2015 | Davenport et al. | |
| 9,198,765 B1 | 12/2015 | Pimenta | |
| 9,198,772 B2 | 12/2015 | Weiman | |
| 9,204,972 B2 | 12/2015 | Weiman et al. | |
| 9,204,974 B2 | 12/2015 | Glerum et al. | |
| 9,211,196 B2 | 12/2015 | Glerum et al. | |
| 9,216,095 B2 | 12/2015 | Glerum et al. | |
| 9,226,836 B2 | 1/2016 | Glerum | |
| 9,271,843 B2 | 3/2016 | Fabian et al. | |
| 9,278,008 B2 | 3/2016 | Perl et al. | |
| 9,283,092 B2 | 3/2016 | Siegal et al. | |
| 9,295,562 B2 | 3/2016 | Lechmann et al. | |
| 9,308,099 B2 | 4/2016 | Triplett et al. | |
| 9,320,613 B2 | 4/2016 | Dmuschewsky | |
| 9,351,848 B2 | 5/2016 | Glerum et al. | |
| 9,358,126 B2 | 6/2016 | Glerum et al. | |
| 9,358,128 B2 | 6/2016 | Glerum et al. | |
| 9,358,129 B2 | 6/2016 | Weiman | |
| 9,370,434 B2 | 6/2016 | Weiman | |
| 9,402,739 B2 | 8/2016 | Weiman et al. | |
| 9,408,708 B2 | 8/2016 | Greenhalgh | |
| 9,414,934 B2 | 8/2016 | Cain | |
| 9,414,936 B2 | 8/2016 | Miller et al. | |
| 9,452,063 B2 | 9/2016 | Glerum et al. | |
| 9,456,903 B2 | 10/2016 | Glerum et al. | |
| 9,474,623 B2 | 10/2016 | Cain | |
| 9,474,625 B2 | 10/2016 | Weiman | |
| 9,480,573 B2 | 11/2016 | Perloff et al. | |
| 9,480,578 B2 | 11/2016 | Pinto | |
| 9,486,325 B2 | 11/2016 | Davenport et al. | |
| 9,486,328 B2 | 11/2016 | Jimenez et al. | |
| 9,492,283 B2 | 11/2016 | Glerum | |
| 9,492,287 B2 | 11/2016 | Glerum et al. | |
| 9,492,288 B2 | 11/2016 | Wagner et al. | |
| 9,510,954 B2 | 12/2016 | Glerum et al. | |
| 9,522,068 B2 | 12/2016 | Goel et al. | |
| 9,539,108 B2 | 1/2017 | Glerum et al. | |
| 9,545,319 B2 | 1/2017 | Farin | |
| 9,554,918 B2 | 1/2017 | Weiman | |
| 9,561,116 B2 | 2/2017 | Weiman et al. | |
| 9,561,117 B2 | 2/2017 | Lechmann et al. | |
| 9,566,168 B2 | 2/2017 | Glerum et al. | |
| 9,579,124 B2 | 2/2017 | Gordon et al. | |
| 9,579,130 B2 | 2/2017 | Oglaza et al. | |
| 9,597,197 B2 | 3/2017 | Lechmann et al. | |
| 9,597,200 B2 | 3/2017 | Glerum et al. | |
| 9,610,175 B2 | 4/2017 | Barreiro et al. | |
| 9,610,176 B1 | 4/2017 | Abdou | |
| 9,615,937 B2 | 4/2017 | Barreiro | |
| 9,655,744 B1 | 5/2017 | Pimenta | |
| 9,888,859 B1 * | 2/2018 | Spangler | A61B 5/4893 |
| 10,105,238 B2 | 10/2018 | Koch et al. | |
| 10,201,431 B2 | 2/2019 | Slater et al. | |
| 2010/0331883 A1 * | 12/2010 | Schmitz | A61B 17/0218 |
| | | | 606/279 |
| 2011/0184422 A1 * | 7/2011 | Mathews | A61M 25/10 |
| | | | 606/90 |
| 2014/0121774 A1 | 5/2014 | Glerum et al. | |
| 2014/0249631 A1 | 9/2014 | Weiman | |
| 2014/0277497 A1 | 9/2014 | Bennett et al. | |
| 2014/0303730 A1 * | 10/2014 | McGuire | A61B 17/8811 |
| | | | 623/17.12 |
| 2015/0066145 A1 | 3/2015 | Rogers et al. | |
| 2015/0265320 A1 | 9/2015 | Hynes et al. | |

(56) References Cited

U.S. PATENT DOCUMENTS

| | | |
|---|---|---|
| 2015/0342586 A1 | 12/2015 | Lim et al. |
| 2016/0051373 A1 | 2/2016 | Faulhaber |
| 2016/0128846 A1 | 5/2016 | Voellmicke |
| 2016/0199194 A1 | 7/2016 | Slater et al. |
| 2016/0270772 A1 | 9/2016 | Beale et al. |
| 2016/0310291 A1 | 10/2016 | Greenhalgh |
| 2017/0042695 A1 | 2/2017 | Foley et al. |
| 2017/0065269 A1* | 3/2017 | Thommen .......... A61B 1/00091 |
| 2017/0105845 A1 | 4/2017 | Glerum et al. |
| 2019/0142407 A1* | 5/2019 | Jung ..................... A61F 2/4611 600/104 |
| 2019/0209154 A1* | 7/2019 | Richter .............. A61B 1/00091 |
| 2020/0015925 A1* | 1/2020 | Scheib ............... A61B 17/0218 |
| 2020/0107824 A1* | 4/2020 | Fleischer ........... A61B 17/0293 |

FOREIGN PATENT DOCUMENTS

| | | |
|---|---|---|
| EP | 3038565 A1 | 7/2016 |
| JP | 6096282 B2 | 3/2017 |
| WO | 2013052807 A2 | 4/2013 |
| WO | 2013109346 A1 | 7/2013 |
| WO | 2013173767 A1 | 11/2013 |
| WO | 2014151162 A1 | 9/2014 |
| WO | 2014164625 A1 | 10/2014 |
| WO | 2017015165 A1 | 1/2017 |
| WO | 2017027277 A1 | 2/2017 |
| WO | 2017035155 A1 | 3/2017 |
| WO | 2017051416 A1 | 3/2017 |

OTHER PUBLICATIONS

Eum, Jin Hwa et al. "Percutaneous biportal endoscopic decompression for lumbar spinal stenosis: a technical note and preliminary clinical results." J Neurosurg Spine 24:602-607, Apr. 2016; published online Jan. 1, 2016.

Innovasive Inc. "Innovasive DualX LLIP expanding IBFD Product Information and Instructions for Use." May 2018, 2 pages.

International Bureau, Written Opinion, PCT Patent Application PCT/US2016/048222 filed Aug. 23, 2016; dated Mar. 2, 2017, 4 pages.

Kim, Jin-Sung et al., "Endoscope-assisted oblique lumbar interbody fusion for the treatment of cauda equina syndrome: a technical note." Eur Spine J (2017) 26:397-403.

* cited by examiner

MULTI-PORTAL SURGICAL SYSTEMS, CANNULAS, AND RELATED TECHNOLOGIES

CROSS-REFERENCE TO RELATED APPLICATION

The present application is a continuation-in-part of U.S. patent application Ser. No. 16/565,403, filed Sep. 9, 2019, and entitled "MULTI-PORTAL SURGICAL SYSTEMS," which is incorporated by reference in its entirety.

TECHNICAL FIELD

The present disclosure relates generally to medical systems and, more particularly, to systems, devices, and methods for performing multi-portal surgical procedures.

BACKGROUND

Individuals often suffer from damaged or displaced spinal discs and/or vertebral bodies due to trauma, disease, degenerative defects, or wear over an extended period of time. One result of this displacement or damage to a spinal disc or vertebral body may be chronic back pain. A common procedure for treating damage or disease of the spinal disc or vertebral body may involve partial or complete removal of an intervertebral disc. An implant (commonly referred to as an interbody spacer) can be inserted into the cavity created where the intervertebral disc was removed to help maintain height of the spine and/or restore stability to the spine. An interbody spacer may also provide a lordotic correction to the curvature of the spine. An example of an interbody spacer that has been commonly used is a fixed dimension cage, which typically is packed with bone and/or bone-growth-inducing materials. Unfortunately, it may be difficult to implant the interbody spacer at the intended implantation site between vertebral bodies. Additionally, conventional surgical techniques can cause a significant amount of trauma at or near the implantation site, which can significantly increase recovery time and lead to patient discomfort. Accordingly, there is a need for improved surgical systems, visualization techniques, and/or related technologies.

DETAILED DESCRIPTION

Figure 1:
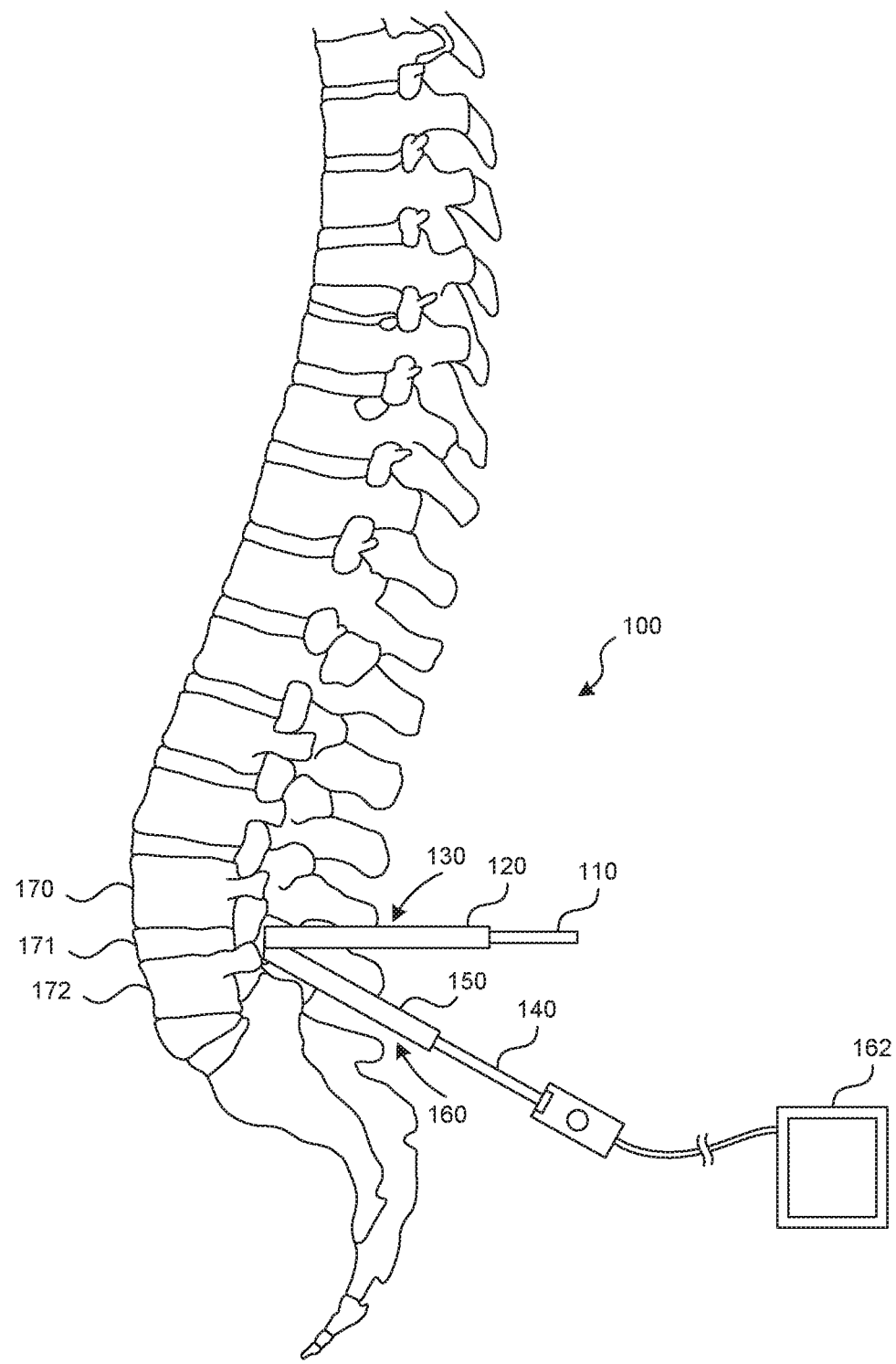
FIG. 1 is a side view of a multi-portal surgical system in accordance with an embodiment of the disclosure.

The following disclosure describes various embodiments of medical systems and devices and associated methods of use. At least some embodiments of a surgical system provide visualization capability. A series of instruments can be delivered via portal sites and used to alter tissue (e.g., shape, crush, separate, cut, debulk, break, fracture, or remove tissue), prepare an implantation site, implant a device, combinations thereof, or the like. Instrument visualization can help a physician prevent or limit injury or damage to non-targeted organs and tissues. In endoscopic-assisted surgeries, devices can be precisely implanted using minimally-invasive techniques to improve outcomes and reduce recovery times. Certain details are set forth in the following description and in FIGS. 1-20 to provide a thorough understanding of such embodiments of the disclosure. Other details describing well-known structures and systems often associated with, for example, surgical procedures are not set forth in the following description to avoid unnecessarily obscuring the description of various embodiments of the disclosure.

A. Overview

At least some embodiments are directed to multi-portal surgical systems. The surgical systems can be used to treat patients with damaged or displaced spinal discs and/or vertebral bodies. The surgical systems can be used to implant a fixed or expandable interbody device to space apart vertebral bodies, restore stability of the spine, provide lordotic correction, combinations thereof, or the like. In spinal fusion procedures, interbody devices can be used alone or in combination with bone, bone-growth-inducing materials, fixation devices (e.g., pedicle screw systems, fixation rods, etc.), or the like. The patient's spine can be visualized using endoscopic techniques to view, for example, the spine (e.g., vertebral spacing, vertebral alignment, etc.), tissue (e.g., damaged or displaced sections of intervertebral cartilage disc, tissue contributing to nerve compression, etc.), instruments and implants before, during, and after implantation, or the like. The visualization can help a physician throughout the surgical procedure to improve patient outcome.

The surgical system can provide access to the surgical site. The implantation site can be prepared by performing a discectomy, interbody preparation procedure, or the like. One or more devices (e.g., implants, fusion devices, etc.) can be delivered and placed within the patient. In some embodiments, decompression procedures can be performed to minimize or reduce pressure applied to nerve tissue and can include removing tissue contributing to stenosis, tissue pushing against nerve tissue, bulging sections of intervertebral cartilage disc, or the like. For example, decompression procedures can be performed to enlarge an epidural space to reduce spinal cord compression.

One surgical method includes positioning a distraction instrument between adjacent vertebrae at a first portal site along the patient to enlarge an intervertebral space. A tissue removal device can be used to clear and prepare the enlarged intervertebral space for implantation. An interbody fusion implant can be delivered into the enlarged intervertebral space. The expanding interbody fusion implant is endoscopically viewed using an endoscopic instrument, which is positioned at a second entrance along the patient. Endoscopic viewing can be used to evaluate whether the expanded interbody fusion implant is at the desired location, assist in delivering bone graft material, or other steps that promote bone healing and facilitate spinal fusion. Other visualization techniques can be used in combination with the endoscopic viewing. For example, fluoroscopy can be used in combination with endoscopic viewing.

In some embodiments, a multi-portal, endoscopy-assisted method for treating a subject includes performing at least a portion of a surgical procedure by using a first portal site. At least a portion of the surgical procedure uses an endoscope positioned via a second portal site spaced apart from the first portal site. The spacing can be selected based on location and accessibility of the treatment site(s), whether along the spine or at another location.

In some embodiments, a multi-portal method for treating a subject's spine includes distracting adjacent vertebrae using a distraction instrument positioned at a first entrance along the subject to enlarge an intervertebral space between the adjacent vertebrae. An interbody fusion implant is delivered into the enlarged intervertebral space. The interbody fusion implant is positioned directly between vertebral bodies of the adjacent vertebrae while being endoscopically viewed using an endoscopic instrument. The endoscopic instrument can be positioned at a second entrance along the subject. The positions of the first and second entrances can be selected based on the accessibility of the implantation site.

In yet further embodiments, a multi-portal method for treating a spine of a subject includes positioning a first cannula at a first portal along the subject. A first vertebral body and a second vertebral body are distracted using one or more distraction instruments, which can extend through the first cannula. The interbody fusion implant can be moved, via the first cannula, toward an intervertebral implantation site between the distracted first and second vertebral bodies. At least a portion of the intervertebral implantation site and at least a portion of the interbody fusion implant can be visualized using an endoscopic instrument positioned at a second portal along the subject.

In some embodiments, a spinal implant delivery instrument includes an elongated body configured to be positioned in a cannula and a distractor assembly. The distractor assembly can be coupled to the elongated body and movable from a delivery state to an expanded state to distract first and second vertebral bodies. In certain embodiments, the distractor assembly in the delivery state is configured for insertion into an intervertebral space between the first and second vertebral bodies and, in the expanded state, is configured to hold apart the distracted first and second vertebral bodies while an interbody fusion implant is delivered into the intervertebral space.

In further embodiments, a spinal implant delivery instrument includes an elongated body configured to be positioned in a cannula and a distractor assembly coupled to the elongated body. The distractor assembly is movable from a delivery state to an expanded state to distract first and second vertebral bodies. The distractor assembly in the delivery state is configured for insertion into an intervertebral space and, in the expanded state, is configured to hold apart the distracted first and second vertebral bodies while an interbody fusion implant is delivered. The interbody fusion implant can be delivered from the distractor assembly and into the intervertebral space. In some embodiments, a driver is detachably couplable to a rotatable connection interface of the interbody fusion implant. The driver can move axially to move the interbody fusion implant directly between the first and second vertebral bodies. The driver is configured to expand the interbody fusion implant from a collapsed configuration to a deployed configuration. The distractor assembly can include a jaw operable to define a delivery gap through which the interbody fusion implant can be delivered.

In some embodiments, a multi-portal method for treating a subject's spine includes inserting multiple cannulas into a subject. The cannulas can be used to identify tissue to, for example, facilitate placement of the cannulas/instruments and/or identify tissue (e.g., targeted tissue, non-targeted tissue, etc.), or the like. The cannulas can be used to circulate (e.g., continuously or intermittently) irrigation fluid (e.g., saline, water, etc.) through and around the surgical site. Tissue-mapping and surgical site irrigation can be performed concurrently or sequentially. In some embodiments, fresh irrigation fluid can be delivered by an irrigation system through a first cannula. The irrigation system can have one or more pumps that generate desired back pressure. To remove the irrigation fluid, another cannula can draw an optional vacuum to suck the irrigation fluid and unwanted material (e.g., blood, bone dust, loose tissue, etc.) out of the subject. Additionally, the pressurized irrigation fluid in the subject can help promote hemostasis. The cannulas can be used to generate desired flows of irrigation fluid.

Irrigation fluid (e.g., flows of irrigation fluid into and/or out of the subject) can be monitored to, for example, facilitate visualization, provide feedback to a clinician, or the like. In some embodiments, irrigation fluid can be circulated periodically based on endoscopic visibility. If the system detects an excess amount of bone dust, for example, the system can automatically circulate irrigation fluid through the surgical site to remove bone dust. In some embodiments, a clinician can control, via a control pedal, hand controls, etc., when irrigation fluid is circulated. Advantageously, the cannulas can have fluid lumens spaced apart from working lumens such that the irrigation fluid flow rates can be increased or decreased without interfering with instruments located in the working lumens. This allows for independent control of instruments and irrigation.

The cannulas can include, without limitation, sensors (e.g., flow sensors), flow diffusers, flow spreaders, valves (e.g., one-way valves), fittings (e.g., fittings for connecting to hoses), connectors, and other fluidic components. For example, proximal ends of cannulas can have one or more fittings for connecting to fluid lines of an irrigation system. Distal ends of cannulas can include nozzles for directing flows in a desired direction. The configuration of the cannulas can be selected based on the desired circulation. For example, to reduce or minimize trauma to tissue positioned immediately distal to the cannula, the cannula can have outlets or nozzles configured to direct fluid laterally away from non-targeted tissue. The cannula can direct a stream of irrigation fluid toward the vacuum cannula. Cannulas can also have one or more expanders, including mechanical expanders, pneumatic expanders, or the like.

In some embodiments, information obtained using cannulas can be used to guide instruments, evaluate the surgical procedure, confirm whether a procedure has been completed, or the like. In embodiments with tissue-identifying probes, the cannulas can be used to identify one or more types of tissue. Nerve-detecting probes can be used to identify nerve tissue, for example. This allows a surgeon to perform procedures while minimizing or limiting the impact to nerve tissue. In some automated detection embodiments, a system can automatically notify a user that the cannula is contacting or adjacent to non-targeted tissue. The surgeon can keep the cannula at a safe location. In some procedures, the cannula is used to map a pathway to a surgical site, a surgical site itself, or other desired location.

The surgeon can manually rotate a cannula to map tissue around and proximate to the distal end of the cannula. In other embodiments, the cannula can have a distal end that automatically rotates for mapping an area. Such a cannula can include one or more motors, actuators, or the like.

In yet other embodiments, a cannula includes an elongated body and a plurality of lumens extending through the elongated body. One of the lumens can be a working lumen configured to allow a surgical instrument to pass therethrough. Another one of the lumens can be a fluid lumen configured to provide a flow of surgical irrigation fluid to/from the surgical site. In some embodiments, the cannula can have additional fluid lumen configured to provide another flow of irrigation fluid.

In multi-portal surgical techniques, two cannulas can be used to circulate irrigation fluid. In some embodiments, a fluid lumen of a first cannula can be connected to an irrigation fluid supply system. Irrigation fluid can flow through a fluid lumen and exit a distal end of a first cannula. The irrigation can flow along the surgical site. The irrigation fluid can be drawn from the surgical site through a fluid lumen of a second cannula. In some embodiments, the first and/or second cannulas can have two or more fluid lumens. Additional lumens can be connected to either the fluid supply system or the fluid return system. In this way, any of the cannulas can be configured to supply or return irrigation fluid. In further embodiments, cannulas can be configured to both supply and return irrigation fluid.

The irrigation fluid supply system can include one or more fluid supply reservoirs, pumps, flow monitors, pressure monitoring devices, flow control mechanisms, or the like. Similarly, the fluid return system can include one or more pumps, pressure monitoring devices, flow control mechanisms, return fluid containers, or the like. The supply and return systems can be components of an irrigation fluid control system. The irrigation fluid control system can provide monitoring, such as flow monitoring, pressure monitoring, etc. In some embodiments, the control system can selectively supply and return fluid through any one of the connected fluid lumens according to the needs of the surgical procedure.

Additionally, cannulas can include one or more detectors, such as tissue-mapping probes. The detectors can be configured to output and/or receive energy to acquire information, identify tissue (e.g., tissue at or near the treatment site), and/or monitor treatment. In some embodiments, the detectors are neuromonitoring electrodes configured to identify nerves using, for example, electromyography techniques. Mapping the location of nerves can be useful to guide the position of the cannula, instruments, or other devices to reduce or avoid nerve tissue injury. The detectors can be connected to a tissue-mapping system programmed to determine locations of tissue. The tissue-mapping system can provide feedback about the location of tissue, including, for example, an audible tone indicating proximity to a nerve or other tissue (e.g., targeted tissue, non-targeted tissue, etc.). In other embodiments, the tissue-mapping system can provide a visual indication of the location of tissue. The visual indication can be, for example, image(s), identifiers of tissue locations overlaid on image data (e.g., still image(s), video, etc.) provided by a visualization instrument, such as an endoscope, fiber optic viewing system, or the like.

In further embodiments, a cannula can include a deployable expander. The expander can be configured to enlarge spaces or working volumes, thereby aiding visibility and/or facilitating the flow of irrigation fluid to or from the cannula. The expander can have a delivery configuration to minimize its profile during insertion into the subject. The expander can be coupled to or part of the distal end of the cannula such that the body of the expander contacts the cannula body. In other embodiments, the expander is coupled to the cannula by a connector mechanism and extendably engaged with the cannula body to extend the expander a distance away from the cannula body, for example, prior to and/or during deployment. In yet other embodiments, the expander is a separate device configured to be delivered through one of the working lumens of the cannula.

The expander can include one or more tissue-mapping probes. These probes can be in place of or in addition to tissue-mapping probes located on a cannula body. The probes can be used to aid the positioning of the cannula, the deployment and/or positioning of the expander, the insertion and use of a surgical instrument, and/or the evaluation of the procedure (e.g., to determine whether a nerve has been damaged or severed).

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

B. Multi-Portal Surgical Systems

FIG. 1 is a side view of a spinal surgical system 100 ("system 100") positioned along a human subject's spine in accordance with an embodiment of the disclosure. The system 100 can include an instrument assembly 130 and a visualization assembly 160. The instrument assembly 130 can be used to perform at least a portion of a surgical procedure while the visualization assembly 160 provides visualization. The instrument assembly 130 can include an instrument 110 and a cannula 120. Ports can be used to facilitate insertion of the instrument assembly 130 and/or visualization assembly 160. For example, the visualization assembly 160 can be positioned in an endoscope port, and the instrument assembly 130 can be positioned in an instrument port.

A series of instruments can be delivered through the cannula 120 to perform a surgical procedure. In some procedures, the instrument 110 can be used to prepare an implantation site by, for example, moving organs or tissue (e.g., moving nerve tissue), removing tissue (e.g., removing the intervertebral disc 171, removing tissue contributing to stenosis, etc.), preparing vertebral bodies (e.g., roughening or shaping vertebral endplates), or the like. The instrument 110 can be removed and a distraction instrument can be delivered through the cannula 120. The distraction instrument can distract adjacent vertebrae 170, 172, thereby enlarging the intervertebral space. An interbody fusion implant can be delivered through the cannula 120 and into the enlarged intervertebral space. In expandable embodiments, the interbody spacer or fusion implant can be expanded to contact vertebral endplates. During the procedure, the visualization assembly 160 can provide endoscopic viewing of delivery paths, organs, tissue (e.g., nerve tissue) implantation sites, interbody fusion devices (e.g., before, during, and/or after delivery), instrument(s), and other areas or features of interest. The position of the portal sites for the instrument assembly 130 and the visualization assembly 160 can be selected based on the procedure to be performed and optical characteristics (e.g., field of view, zoom capability, etc.) of the visualization assembly 160, as discussed in connection with FIG. 4.

With continued reference to FIG. 1, the visualization assembly 160 can include a visualization device 140 and a cannula 150. The cannula 150 can help a physician when switching between visualization devices. In some embodiments, the visualization assembly 160 can be used without the cannula 150. For example, the visualization device 140 in the form of a low-profile fiber optic endoscope positioned directly through an incision, an endoscopic port, or the like. The visualization device 140 can include one or more endoscopes having, without limitation, fiber optics (e.g., optical fibers), lenses, imaging devices, working lumens, light sources, controls, or the like for direct viewing or viewing via a display 162. In some embodiments, the visualization device 140 can include a lumen through which fluid flows to irrigate the surgical site. For example, saline, or another suitable liquid, can be pumped through the visualization device 140 to remove tissue (e.g., loose tissue, bone dust, etc.) or other material impairing visualization.

The visualization device 140 can illuminate the body cavity and enable high-resolution video visualization. A light source (e.g., a laser, light-emitting diode, etc.) located near or at the proximal end of the fiber optics can be used to transmit light to the distal end and provide illuminating light. This enables a surgeon to safely navigate into the subject's body and to illuminate specific body anatomy to view vertebral spacing, vertebral structures, nerves, bony buildup (e.g., buildup that could be irritating and pressing against nerves contributing to nerve compression), etc. In some embodiments, visualization optics for vision and illumination are included within the distal tip of the visualization device 140. The configuration and functionality of the visualization device 140 can be selected based on the desired field of view, viewing resolution, pan/zoom functionality, or the like.

Figure 3:
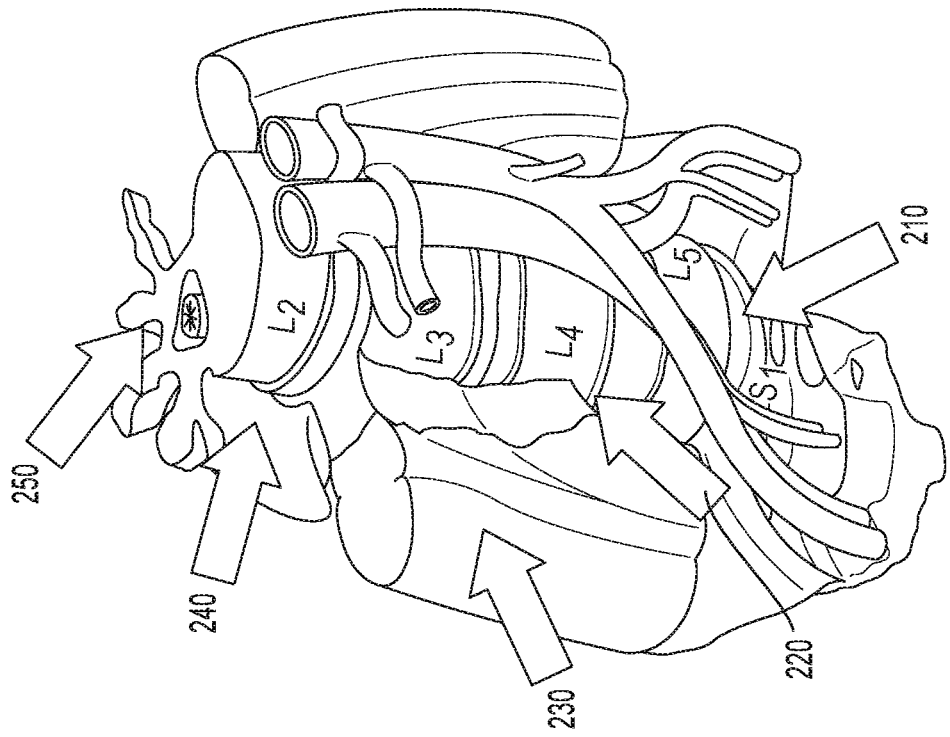
FIG. 3 is an isometric view of the lumbar spine of FIG. 2.
Figure 2:
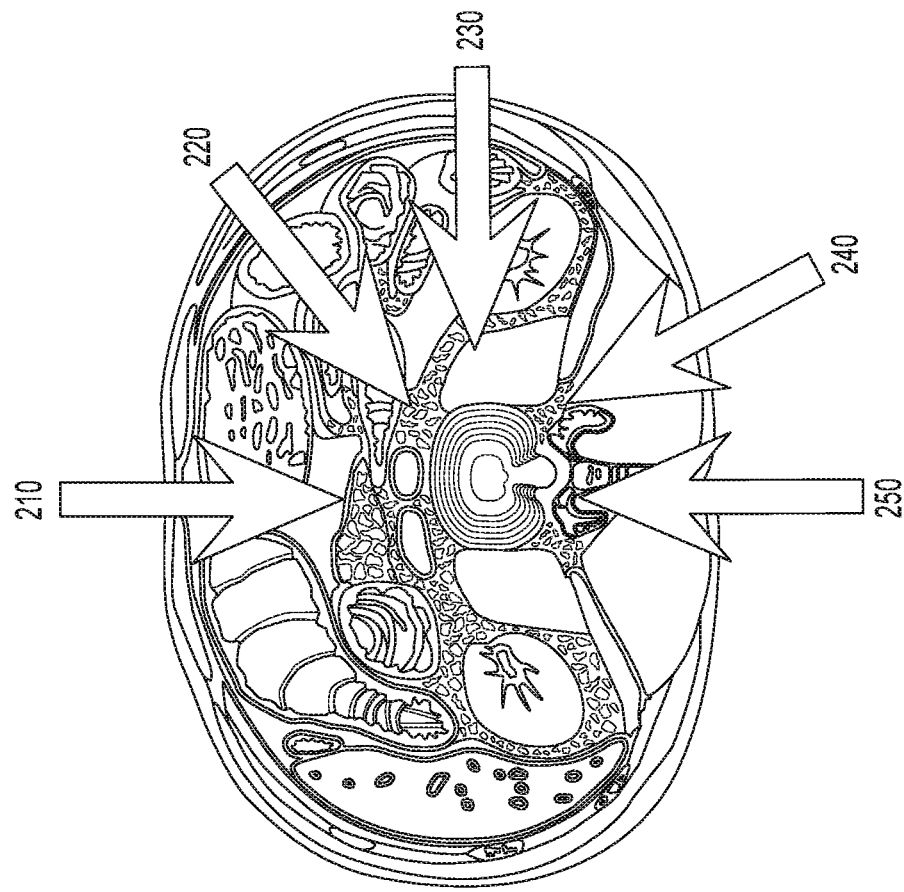
FIG. 2 is a schematic top plan view showing surgical approaches to a lumbar spine for performing interbody fusion procedures.

FIG. 2 is a schematic top plan view along the lumbar spine of a human and illustrates example approaches for performing interbody fusion procedures suitable for the system 100 of FIG. 1. FIG. 3 is an isometric view of the lumbar spine of FIG. 2. Referring to FIGS. 2 and 3, surgical instruments can be delivered via different paths, including an anterior lumbar interbody fusion (ALIF) path 210, an oblique lumbar interbody fusion (OLIF) path 220, a lateral or extreme lateral lumbar interbody fusion (LLIF or XLIF) path 230, a transforaminal lumbar interbody fusion (TLIF) path 240, and a posterior lumbar interbody fusion (PLIF) path 250. Example TLIF and PLIF procedures are discussed in connection with FIGS. 4-6.

With continued reference to FIGS. 2 and 3, the number and configuration of interbody fusion devices can be selected based on the fusion procedure to be performed. In one example TLIF procedure, the transforaminal path 240 may be employed to implant a single small expandable or non-expandable interbody spacer at the intervertebral space. In one example PLIF procedure, two interbody spacers can be delivered along the posterior path 250 and implanted at the intervertebral space. The two interbody spacers can cooperate to keep the vertebral bodies at the desired spacing and may be larger than the TLIF spacer. Additionally, multiple interbody spacers can provide lordotic correction by providing support at different heights. In one example LLIF procedure, a single relatively large interbody spacer can be delivered along the lateral path 230 and implanted to provide asymmetrical support. In one example ALIF procedure, an asymmetric interbody spacer can be delivered along the anterior path 210 to provide support consistent with lordosis at that portion of the spine. Lateral approaches, transforaminal approaches, and anterior approaches can be used to access the cervical spine, thoracic spine, etc. The number of instruments, configurations of instruments, implants, and surgical techniques can be selected based on the condition to be treated.

Figure 4:
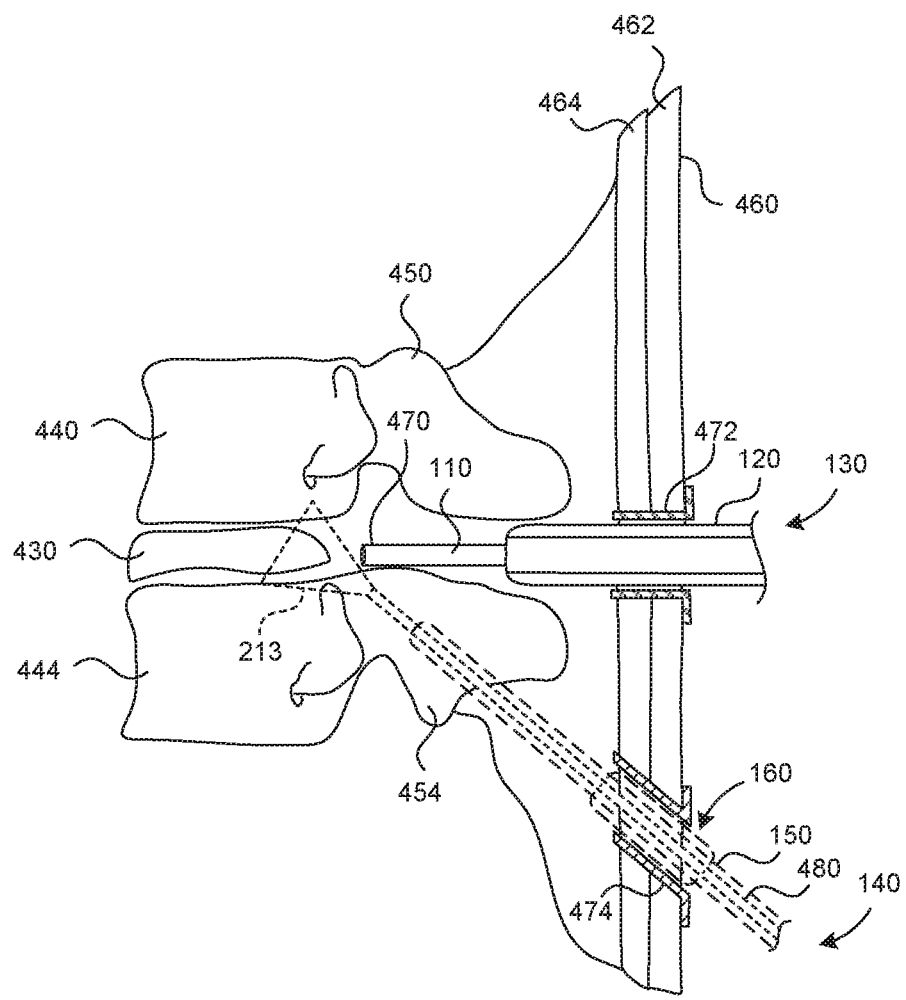
FIG. 4 is a side view of a tissue removal device positioned between adjacent vertebrae and a visualization device positioned to visualize a working area in accordance with an embodiment of the disclosure.

FIG. 4 is a detailed side view of the instrument assembly 130 positioned to perform a TLIF or PLIF procedure in accordance with embodiments of the disclosure. The instrument assembly 130 can extend through a port 472, and the visualization assembly 160 can extend through a port 474. The illustrated instrument assembly 130 can extend through the subject's skin 460, through subcutaneous tissue 462, and adjacent to or through supraspinal ligament 464. The visualization assembly 160 has a field of view 213 suitable for viewing the spinal column and can be positioned using, for example, a transforaminal approach, a posterior approach, or a lateral approach. The illustrated visualization assembly 160 is positioned to enable viewing an intervertebral disc 430 and a tissue removal tip 470 of the instrument 110, which is illustrated between spinous processes 450, 454 of vertebrae 440, 444, respectively. Fluoroscopy, MR imaging, CT imaging, direct visualization, or other visualization techniques can be used in addition to or in lieu of the endoscopic viewing.

The tissue removal tip 470 can be advanced in the anterior direction to remove the intervertebral disc 430, or other unwanted tissue, including, without limitation, tissue bulging from disc 430 (or other discs), bone (e.g., lamina, lateral recesses, facets including the inferior facets, etc.), bone spurs (e.g., bone spurs associated with osteoarthritis), tissue of thickened ligaments, spinal tumors, displaced tissue (e.g., tissue displaced by a spinal injury), or tissue that may cause or contribute to spinal nerve compression. The instrument 110, as well as other instruments (e.g., rongeurs, debulkers, scrapers, reamers, dilators, etc.), can be used to perform one or more dilation procedures, decompression procedures, discectomies, microdiscectomies, laminotomies, or combinations thereof. In procedures for treating stenosis, the instrument 110 can be used to remove tissue associated with central canal stenosis, lateral recess stenosis, and/or other types of stenosis. In some decompression procedures, the instrument 110 can be a tissue removal device used to, for example, remove bone, separate the ligamentum flavum from one or both vertebrae 440, 444, cut or debulk the ligamentum flavum, remove loose tissue, and remove at least a portion of the intervertebral disc 430. Each stage can be performed with a different instrument. Instruments can be selected to treat, without limitation, spinal nerve compression (e.g., spinal cord compression, spinal nerve root compression, or the like), spinal disc herniation, osteoporosis, stenosis, or other diseases or conditions.

The instrument 110 and the visualization device 140 can be positioned along different paths. For example, the instrument 110 can be positioned along a posterior path, whereas the visualization device 140 can be positioned along a transforaminal or oblique path. The ports 472, 474 are positioned at different superior-inferior positions, and the port 472 is positioned directly posterior to the treatment site such that a longitudinal axis of the tissue removal device 110 lies in a plane that is generally parallel to a transverse plane of the subject. The visualization device 140 can be, without limitation, an endoscopic instrument that includes fiber optics 480 suitable to image the ligamentum flavum, spinal cord, nerves branching from spinal cord, ligament, vertebrae 440, 444, intervertebral disc 430, or any other features or anatomical structures of interest while the instrument 110 removes tissue (e.g., bone from the vertebrae 440, 444 or tissue intervertebral disc 430).

Figure 5:
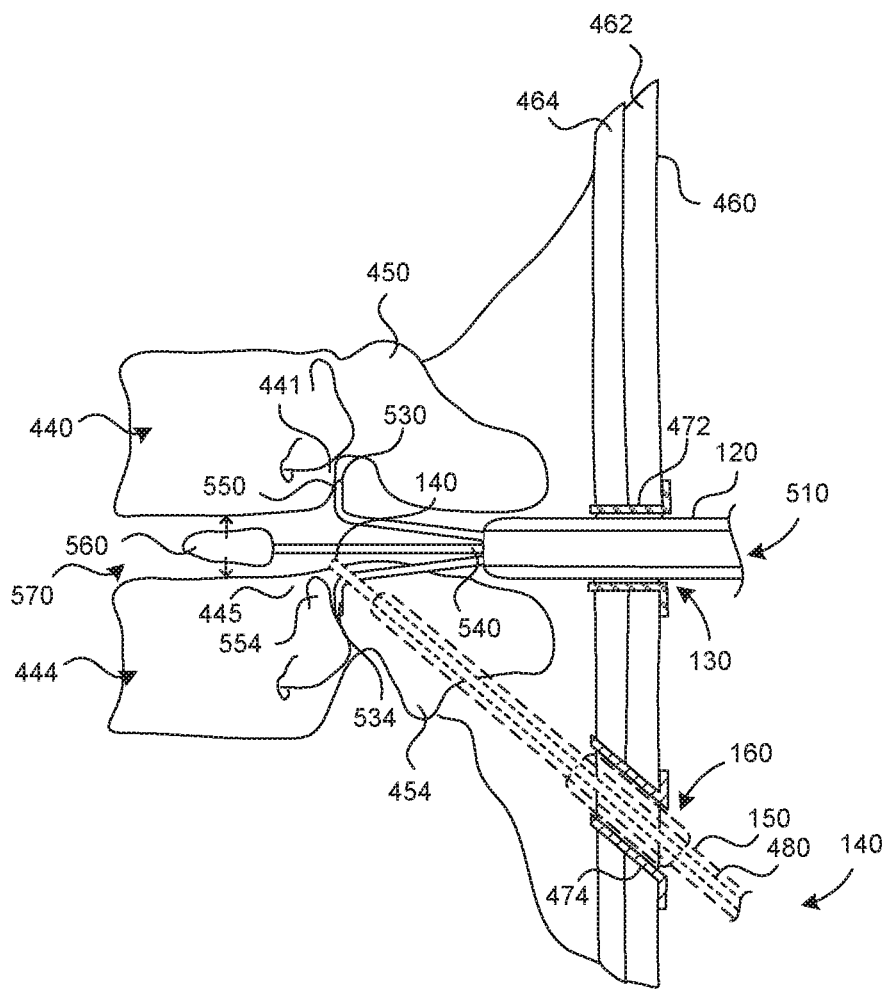
FIG. 5 is a side view of a distraction instrument with a collapsed expansion element positioned at an intervertebral space and a visualization device in accordance with an embodiment of the disclosure.

FIG. 5 is a side view of a distraction instrument with a collapsed expansion element positioned between two vertebrae after an intervertebral disc has been removed in accordance with an embodiment of the disclosure. A distraction instrument 510 is positioned in the cannula 120 and has positioners or stops 530, 534 and an expander or distractor head 560 ("expander 560"), illustrated in a partially expanded state, configured to push apart the adjacent vertebrae 440, 444. Expansion of the expander 560 and the positioners 530, 534 can be viewed endoscopically with the visualization device 140.

The positioners 530, 534 are configured to help position the expander 560 insertable into an intervertebral space 570. For example, the positioner 530 can contact an inferior vertebral notch 550 of the vertebral body 441, and the positioner 534 can contact a superior vertebral notch 554 of the vertebral body 445. An elongate member 540 can be extended or contracted to position the expander 560 at a desired location, while the positioners 530, 534 can remain relatively stationary relative to the vertebral bodies 441, 445. Throughout this process, the visualization device 140 can be used to view the positioners 530, 534, the elongate member 540, and/or the expander 560. A physician can confirm the condition of expander 560 relative to anatomical features prior, during, and after expansion. This ensures that the expander 560 contacts desired regions of the spinal column. The expander 560 can be deployed to push against endplates of the adjacent vertebrae 440, 444, thereby enlarging the intervertebral space 570.

The positioners 530, 534 can include spikes, protrusions, or other movement-inhibiting elements. In some embodiments, anchors or protrusions can be connected directly to the elongate member 540 and can be deployed to engage the endplates. The configuration, number, and position of the positioners can be selected based on the desired positioning relative to the spinal column.

The elongate member 540 is connected to the expander 560 and can be a rod with one or more lumens through which fluid flows. Fluid (e.g., saline, gas, or another suitable fluid) can be pumped through the elongate member 540 to inflate the expander 560. For fluoroscopy, the fluid can include a contrast media. The expander 560 can include, without limitation, one or more inflatable members, balloons, mechanical expanders, wedging devices, or the like. Arrows indicate one of the many possible directions of expansion, and the direction of expansion of the expander 560 is not limited to bidirectional expansion.

The distraction instrument 510 can also deliver an interbody fusion implant and serve as a driver instrument. The distraction instrument 510 can have a shaft connectable to the interbody fusion implant. The shaft can be rotated to deploy the interbody fusion implant. U.S. Pat. Nos. 8,632, 594, 9,308,099, 10,105,238 and 10,201,431, which are hereby incorporated by reference and made a part of this application, disclose driver components that can be incorporated into the distraction instrument 510.

Figure 6:
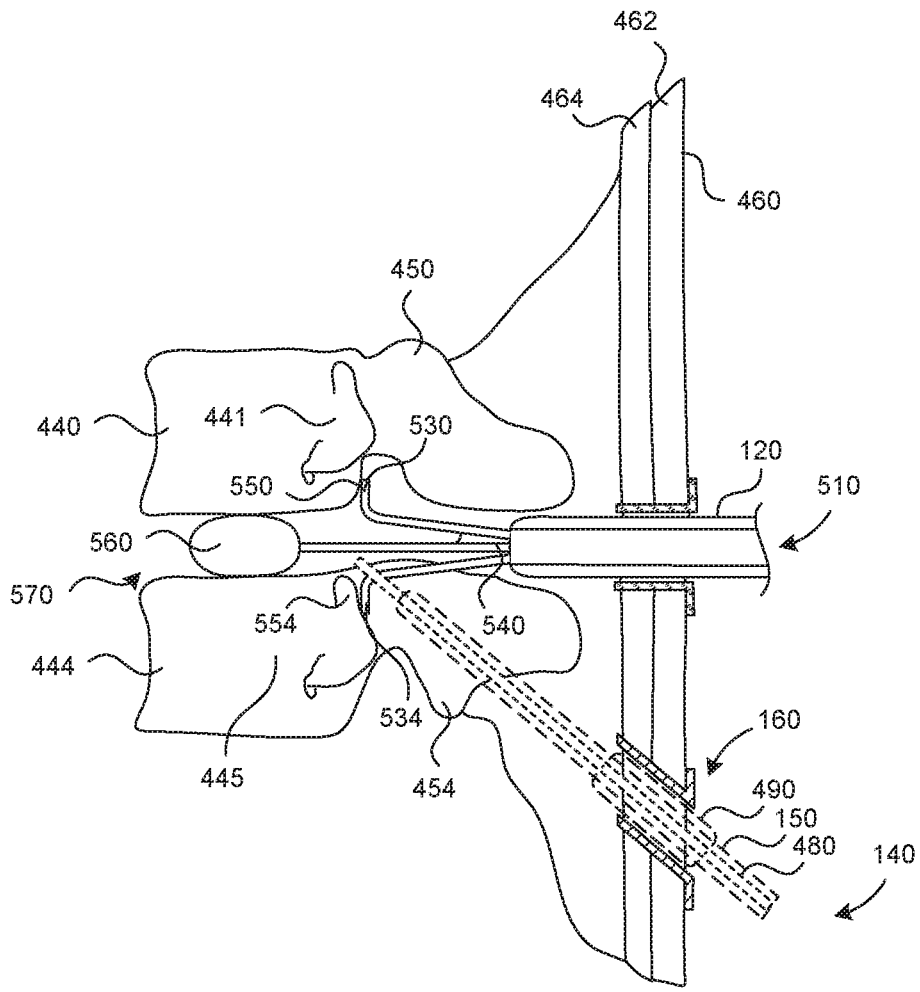
FIG. 6 is a side view of the distraction instrument with the inflated expansion element contacting endplates of vertebral bodies in accordance with an embodiment of the disclosure.

FIG. 6 is a side view of the distraction instrument 510 with an inflated expansion element 560 holding apart the vertebral bodies 441, 445. The level of expansion of expander 560 can be increased or decreased to increase or decrease, respectively, the pressure applied to the endplates. The expander 560 can include one or more roughened surfaces, spikes, protrusions, or other features capable of roughening, abrading, scraping, or otherwise affecting tissue. In some embodiments, the expander 560 has a plurality of protruding spikes that can be used to roughen the opposing vertebral endplate surfaces to help limit or substantially prevent migration of an implanted device. The expander 560 can be collapsed and removed. Another expander can be inserted into the already-expanded intervertebral space 570 to further distract the vertebrae 440, 444. In this manner, the vertebrae can be sequentially distracted in a controlled manner until a desired amount of separation is achieved.

The expander 560 can hold apart the distracted second vertebral bodies 441, 445 while an interbody fusion implant is delivered through the distraction instrument 510 and into the intervertebral space 570. The interbody fusion implant can be positioned adjacent to the deployed expander 560, which can be removed after, for example, deploying the interbody fusion implant.

The configuration of the instruments can be selected based, at least in part, on the distance from the portal sites to the treatment site. The surgical procedure can be selected based on the steps to be performed. For example, TLIF and PLIF surgery can include a decompression procedure in which tissue along the posterior region of the spine is removed in contrast to an ALIF procedure in which no such decompression procedure is performed. The systems and techniques discussed in connection with FIGS. 4-6 can be modified to perform other types of procedures, including non-spine procedures.

Figure 7:
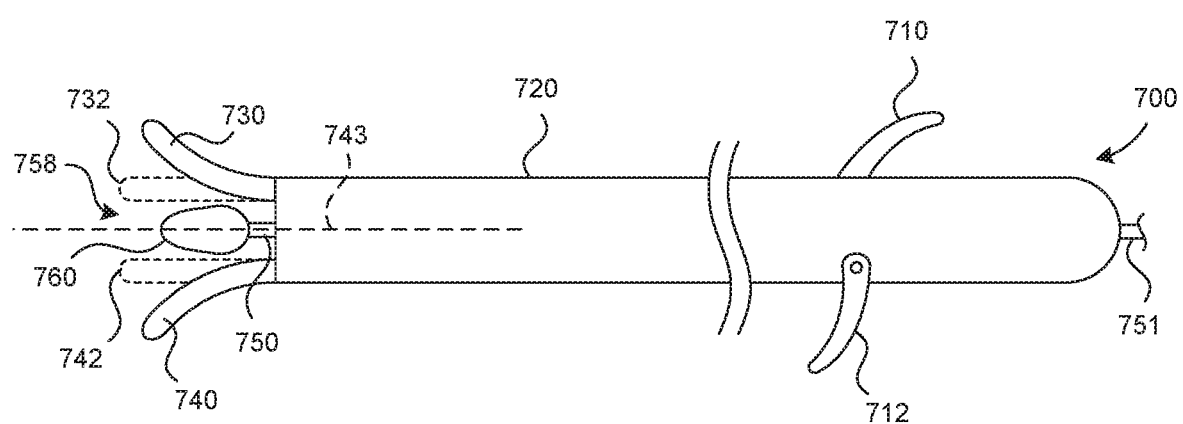
FIG. 7 is a side view of a distraction instrument with an expansion element in accordance with an embodiment of the disclosure.

FIG. 7 is a side view of a distraction instrument 700 with an expansion element in accordance with an embodiment of the disclosure. The instrument 700 can include control elements 710, 712, an elongated body 720, positioners 730, 740, and an expander assembly 758. The control elements 710, 712 can be operated to deploy the positioners 730, 740 and/or expander assembly 758. For example, a user can manually rotate the control elements 710, 712 to independently deploy the respective positioners 730, 740. For example, the control element 710 can be used to rotate the positioners 730, 740 away from undeployed positions 732, 742 (illustrated in dashed line) and a longitudinal axis 743 of the instrument 700 and toward the illustrated outwardly deployed positions.

The distraction instrument 700 can be used in a similar manner as described in connection with FIGS. 5 and 6. For example, the deployed positioners 730, 740 can rest against adjacent vertebrae. The expander assembly 758 has an expander or distractor head 760 ("expander 760") positionable at a desired location suitable for distracting the vertebrae. The expander assembly 758 can include an elongated body 750 fluidically connected to a fluid line 751. The expander 760 can be mounted to the distal end of the elongated body 750 such that fluid can be pumped through the fluid line 751, through the elongated body 750, and into the expander 760.

Figure 8:
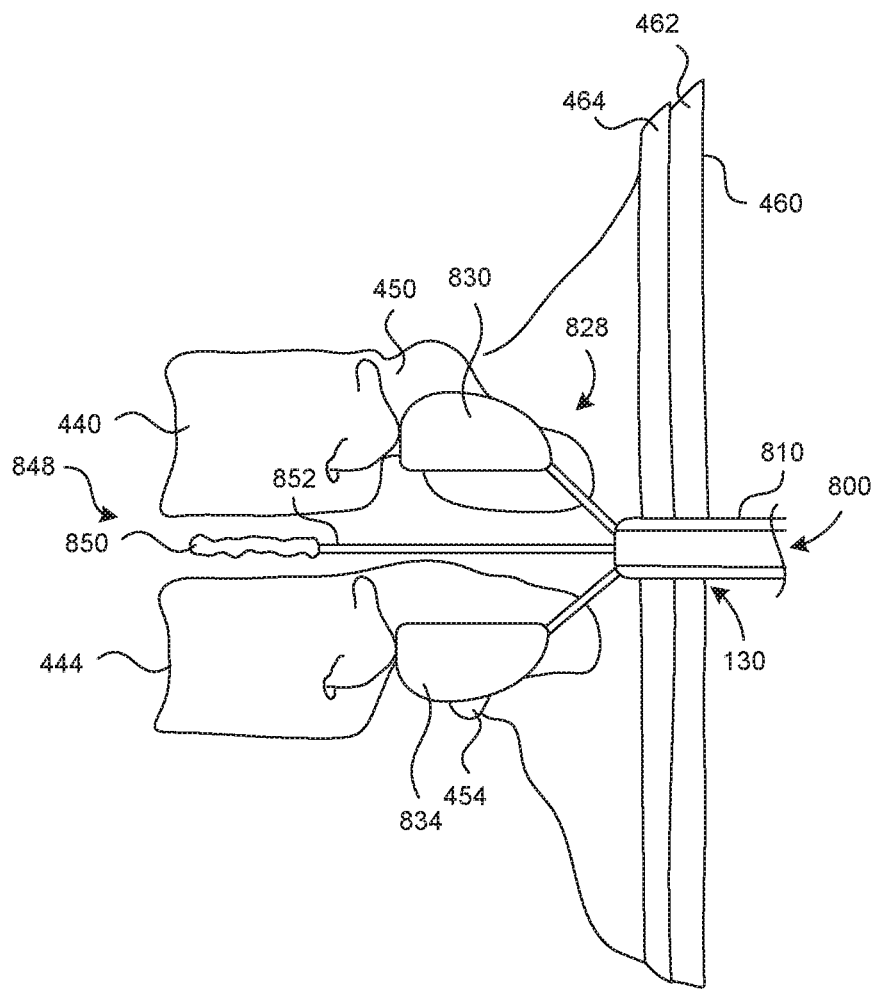
FIG. 8 is a side view of an instrument positioned between two vertebrae in accordance with an embodiment of the disclosure.

FIG. 8 is a side view of an instrument 800 positioned to distract adjacent vertebrae in accordance with an embodiment of the disclosure. A description of the instruments discussed in connection with FIGS. 4-7 applies equally to the instrument 800 unless indicated otherwise.

The instrument 800 can include an access device or cannula 810 and a distraction assembly 828. The cannula 810 can serve as an access device through which the distraction assembly 828 can be delivered. The distraction assembly 828 can include positioners 830, 834 configured for atraumatic contact with the spinal column. The positioners 830, 834 can be inflatable members (e.g., inflatable balloons), mechanically expanded members, or other types of elements. The positioners 830, 834 can be configured to contact vertebral bodies, transverse processes, spinous processes, or the like. The distraction assembly 828 can further include an expandable assembly 848 with an expander 850 and an elongated body 852. The illustrated expander 850 is in a collapsed, deflated configuration or state. The expander 850 can be expanded/inflated in a manner similar to the expander 560 discussed in connection with FIGS. 5 and 6. A visualization device can be used to view the expander 850, positioners 830, 834, or other features of the instrument before, during, and/or after the distraction process. In some embodiments, the distraction assembly 828 can function as a jaw in which the positioners 830, 834 can be used to grip or define a delivery gap. Additionally or alternatively, the positioners 830, 834 can be inserted into spaces (e.g., cavities) and then moved apart to expand the spaces.

Figure 9A:
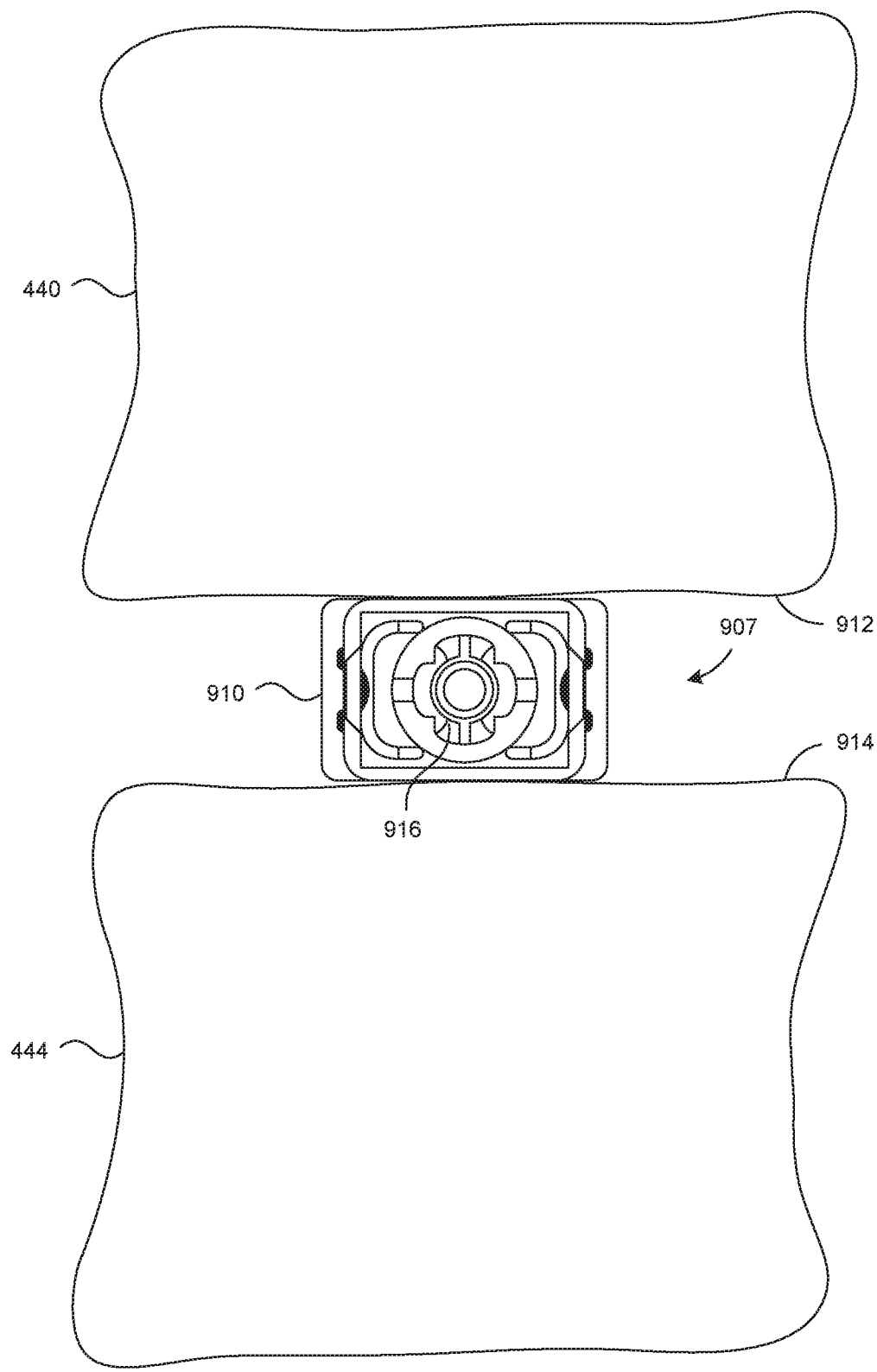
FIGS. 9A, 9B, and 9C are views from an anterior direction of a subject's spine with an interbody spacer positioned between vertebrae in accordance with an embodiment of the disclosure.
Figure 9B:
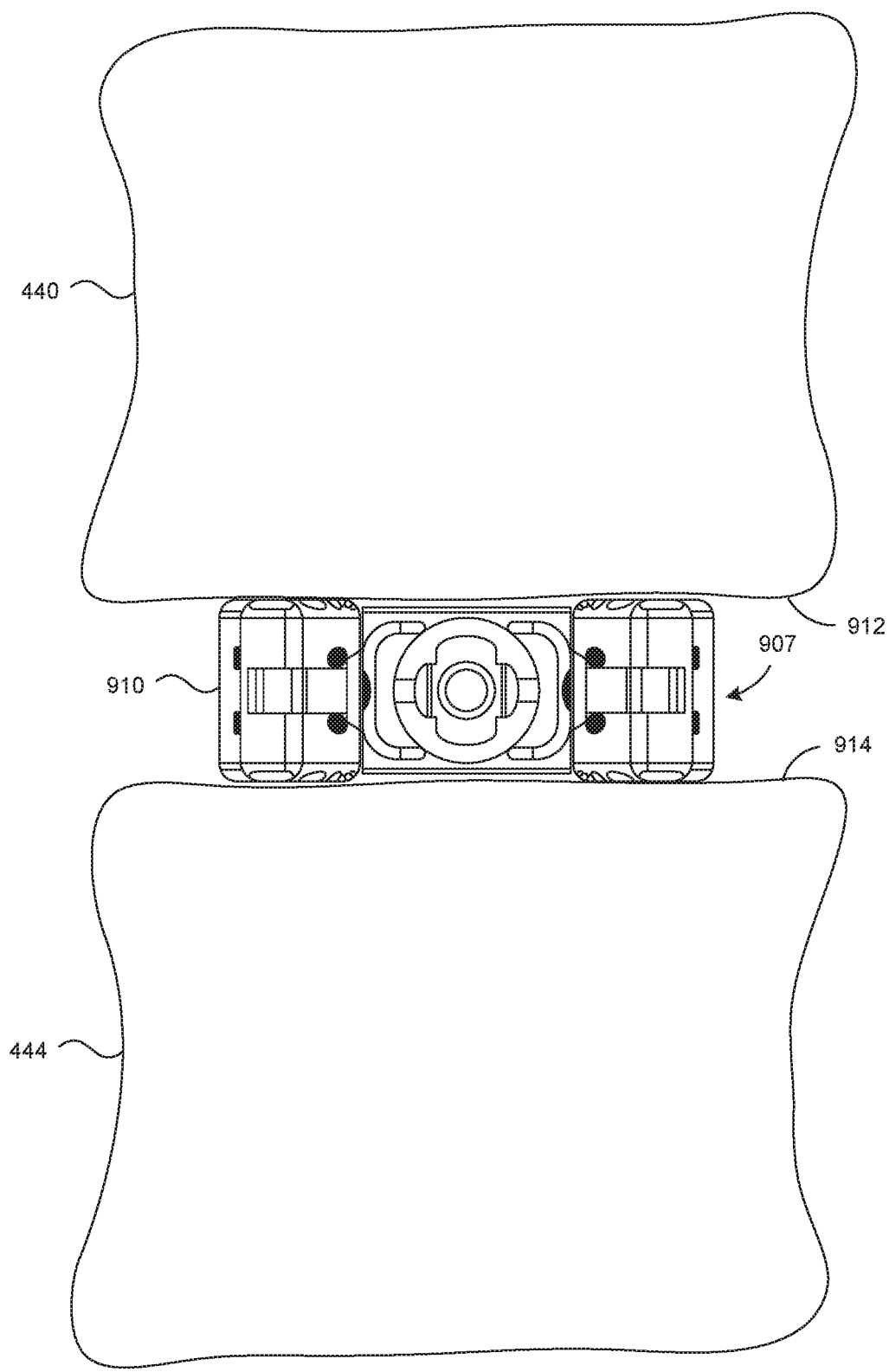
Figure 9C:
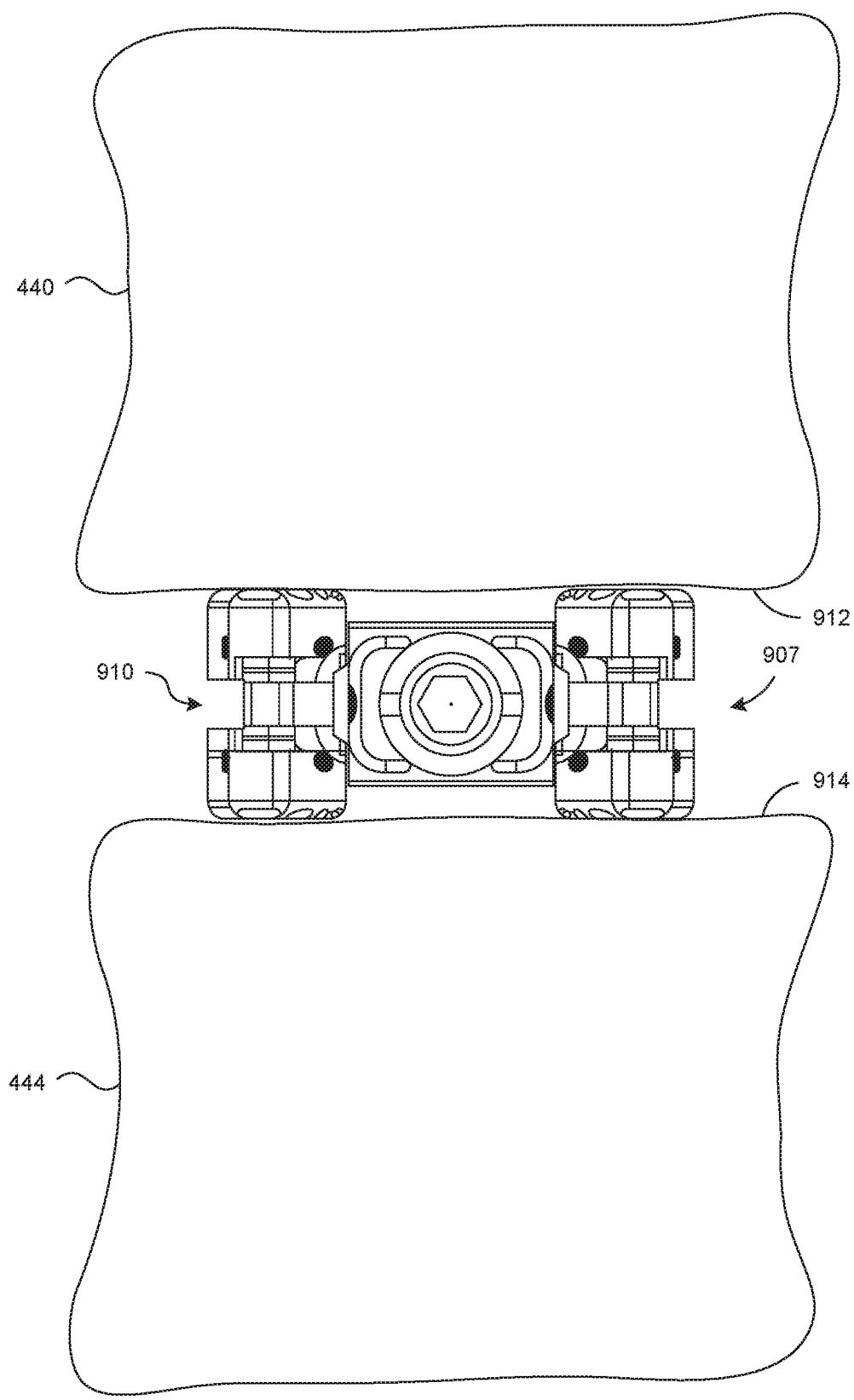

FIGS. 9A-9C are anterior views from an anterior direction of a subject of an interbody spacer 910 between two vertebrae in accordance with an embodiment of the disclosure. In FIG. 9B, the interbody spacer 910 is in a laterally expanded configuration. In FIG. 9C, the interbody spacer 910 is in a laterally and vertically expanded configuration. In general, the interbody spacer 910, in a collapsed configuration, can be delivered into an intervertebral space. After endoscopically viewing the position of the interbody fusion implant, the implant can be moved from the collapsed configuration (FIGS. 9A and 10A) to an expanded configuration (FIGS. 9C and 10B). The expansion (e.g., lateral expansion, vertical expansion, combinations thereof, etc.) can be viewed using the endoscopic instrument. The interbody spacer 910 can be, without limitation, an implant, an interbody fusion implant, or the like. Details of the operation of the interbody spacer 910 are discussed in detail below.

Referring now to FIG. 9A, the intervertebral disc has been removed from the intervertebral space 907. The interbody spacer 910 can be delivered through a cannula, such as the cannula 120 of FIGS. 1-7 or the cannula 810 of FIG. 8, to position the collapsed interbody spacer 910 directly between endplates 912, 914 of the vertebrae 440, 444, respectively. The position of the collapsed interbody spacer 910 can be confirmed via endoscope viewing. If the interbody spacer 910 is at an undesired position, the interbody spacer 910 can be moved to another position. Once again, endoscopic viewing can be used to confirm the final position of the interbody spacer 910.

FIG. 9B shows the interbody spacer 910 after it has been laterally expanded under endoscopic viewing. Advantageously, if the expansion process causes unwanted displacement of the interbody spacer 910, the user can reposition the interbody spacer 910.

FIG. 9C shows the interbody spacer 910 after it has been vertically expanded against endplates 912, 914 of the vertebrae 440, 444, respectively. After full expansion, the interbody spacer 910 can be locked to prevent collapse. Optional material can be delivered to the intervertebral space 907 to promote or facilitate fusion. For example, material can be delivered into the intervertebral space 907 via a delivery instrument 920 (FIG. 10A) connected to the interbody spacer 910. The material can be bone, bone-growth-inducing materials, cement, or other suitable material. The bone-growth-inducing materials can be configured to promote bony arthrodesis. In some procedures, the material is delivered through the passageway of the delivery or driver instrument. In other procedures, the material can be delivered via a separate instrument. In some procedures, multiple interbody spacers are implanted at the intervertebral space 907. Details of delivery instruments are discussed in connection with FIGS. 10A and 10B.

Figure 10A:
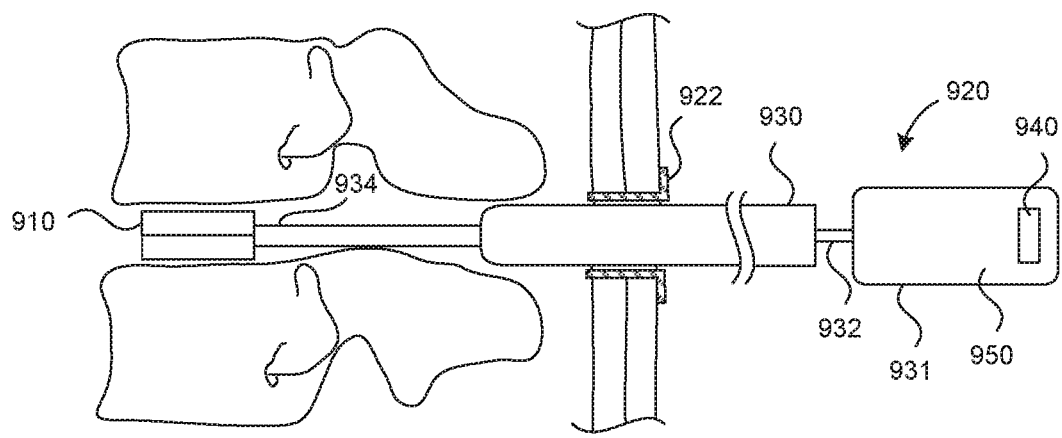
FIG. 10A is a side view of the interbody spacer in a collapsed configuration.
Figure 10B:
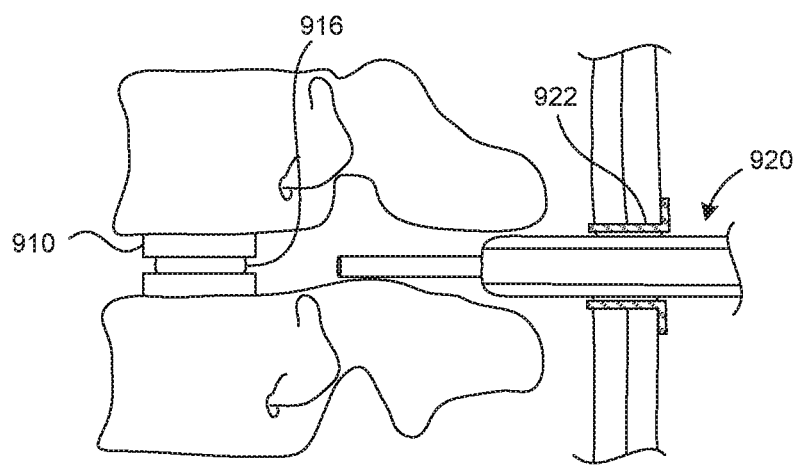
FIG. 10B is a side view of the interbody spacer in an expanded configuration.

Referring to FIG. 10A, the interbody spacer 910 and delivery instrument 920 can be delivered through a port 922, with or without the use of a cannula 930. The instrument 920 can include a handle assembly 931, an elongated body 932, and a connecter 934. The handle assembly 931 can include a grip 950 and one or more control elements 940 operable to control operation of the interbody spacer 910 and control decoupling from the interbody spacer 910. In some embodiments, the control elements 940 can include one or more dials, levers, triggers, or other movable elements. The elongated body 932 is connected to the handle 950 and extends to the connecter 934. The elongated body 932 can serve as a driver instrument and can include one or more rods, shafts, or other elements used to operate the interbody spacer 910. In some embodiments, a driver instrument is inserted through the delivery instrument 920 and into engagement with the interbody spacer 910. The driver instrument can be rotated to gradually and controllably deploy the interbody spacer 910. The features, configuration, and functionality of the connector 934 can be selected based on the configuration of the interbody spacer 910.

FIG. 10B is a side view of the expanded interbody spacer 910 after the delivery instrument 920 has been separated from a connection feature or connection interface 916 ("connection feature 916") of the interbody spacer 910. The expanded interbody spacer 910 can be locked in the expanded configuration. To reposition the interbody spacer 910, the delivery instrument 920 can be reconnected to the interbody spacer 910 and operated to unlock and collapse the interbody spacer 910. The delivery instrument 920 can be used to move the collapsed interbody spacer 910.

The delivery instrument 920 can include one or more distal connection elements or features for detachably coupling to the interbody spacers. The connection elements can be a polygonal connection (e.g., a hexagonal protrusion) received by a complementary polygonal recess or feature of the interbody spacer 910. Other connections can be used to detachably couple the delivery instrument 920 to the interbody spacer 910. U.S. Pat. Nos. 8,632,594, 9,308,099, 10,105,238 and 10,201,431, which are hereby incorporated by reference, disclose delivery instruments, interbody spacers, connection features, and methods of operating delivery instruments and deploying interbody spacers. The delivery instrument 920 can be a delivery instrument and include features disclosed in U.S. Pat. Nos. 8,632,594, 9,308,099, 10,105,238 and 10,201,431. Other types of implantable devices and delivery instruments can be utilized. The configuration of the implant and corresponding delivery instruments can be selected based on the procedure to be performed.

Figure 11:
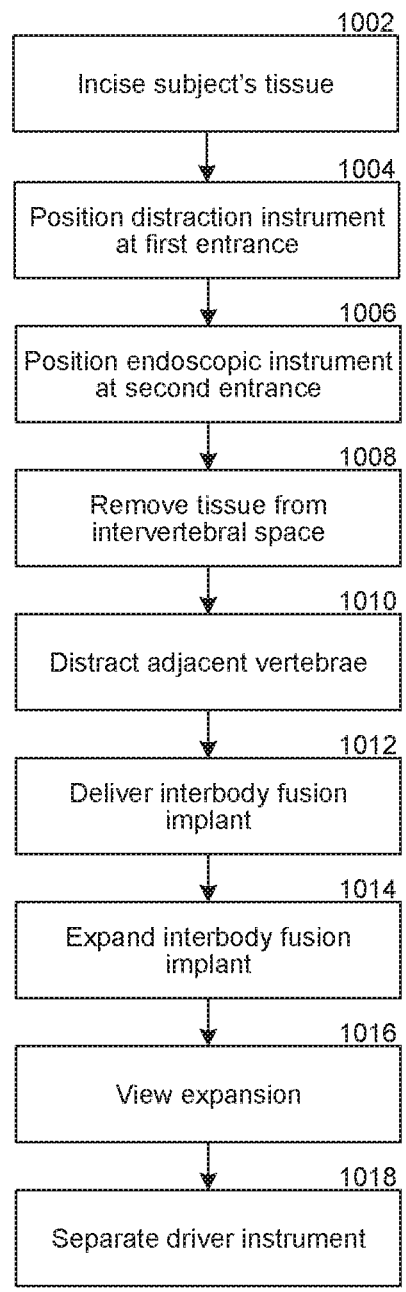
FIG. 11 is a flow diagram illustrating a method for performing a spine surgery in accordance with an embodiment of the disclosure.

FIG. 11 is a flow diagram illustrating a method for treating a subject in accordance with an embodiment of the disclosure. In block 1002, incisions can be made in the subject's tissue to create first and second portal sites (i.e., entrances). In some embodiments, the first and second entrances can be positioned on the same side of the subject's midsagittal plane. In other embodiments, the first and second entrances can be positioned on opposite sides of the subject's midsagittal plane. In yet other embodiments, the incisions can be made along the subject's midsagittal plane.

Ports can be installed in each of the entrances. The sizes of the ports can be selected based on the size of the incision and characteristics of the tissue at the port site. For example, a tubular body of the port can be sufficiently long to extend through the subject's skin, fascia, and muscle. An access opening of the port can be sufficiently large to allow instruments to be inserted into and through the ports, which can prevent or inhibit tearing of tissue. Instruments can be delivered through the incisions into the patient without utilizing ports. Such instruments can have relatively small diameters to limit or inhibit tearing of the tissue around the incision. In some procedures, ports can be installed in some incisions and instruments can be installed in other incisions without ports. A physician can determine whether to install ports based on the instruments to be utilized and the position of the incisions.

In block 1004, a distraction instrument can be positioned at the first portal site by inserting the distraction instrument through, for example, an installed port. In some procedures, a cannula can be positioned in the port and the distraction instrument can be delivered through the lumen of the cannula. In other embodiments, the distraction instrument can be inserted directly into the port without utilizing the cannula. Utilization of distraction instruments and cannulas are discussed in connection with FIGS. 5-8.

In block 1006, a visualization device can be positioned at a second portal site by delivering the visualization device through a port. The visualization device can be installed with or without use of the cannula. Utilization of a cannula and a port are discussed in connection with FIGS. 1-7. In some embodiments, the visualization device can be a low-profile fiber optic visualization system deliverable through a portal site in the form of a small incision. In these procedures, a cannula may not be used since the visualization device has a small diameter. The visualization device can be kept at the same portal site throughout most of the surgical procedure period in which the spine is altered. For example, the visualization device can be positioned at a single portal site for at least 80% or 90% of the surgical period in which instruments are positioned in the subject. The visualization device can be positioned within the subject such that an interbody fusion device is capable of being implanted without removing the endoscope from the subject. This can reduce the overall surgery time.

A steerable visualization device can be used to facilitate navigation around anatomical features. The steerable visualization device can include a fiberoptic scope, or a flexible or rigid instrument with one or more illumination elements (e.g., fiber-optics for illumination) or imaging elements (e.g., charge-coupled devices for imaging) suitable for visualizing the interior of otherwise inaccessible sites. In some embodiments, the visualization device can be rod-lens endoscopes with an outer diameter equal to or smaller than about 2 mm, 3 mm, 4 mm, 5 mm, 6 mm, 8 mm, or 10 mm; and a length equal to or shorter than about 15 cm, 20 cm, 30 cm, or 40 cm. The device can also have connectors (e.g., electrical connectors, fluidic connectors, etc.), access ports (e.g., access ports connected to lumens (e.g., lumens through which instruments can pass), or the like. In embodiments with an angled lens, the visualization instrument can have approximately 15 degree, 30 degree, or 45 degree lens angles, which are angled toward a light source. In other angled lens embodiments, the visualization instrument can have an approximately 15 degree, 30 degree, or 45 degree lens angled away from a light source. The angle of the lens can be selected based on the area to be viewed. In some posterior or lateral spinal procedures, a 0 degree lens can provide a wide-angle view suitable for viewing nerve roots, the spinal cord, and intervertebral space. A 30 or 45 degree lens endoscope angled toward the light source can be used to provide an angled view toward, for example, the midsagittal plane to view, for example, the spinous processes, spinal cord, central regions of the intervertebral space, or the like. A 30 or 45 degree lens endoscope angled away from the light source can be used to provide an angled view toward the lateral features or the spine, such as nerve roots at the neural foramen, side regions of the intervertebral space, or the like.

In some procedures, multiple visualization instruments are utilized. In one procedure, multiple visualization instruments are positioned within the same port, which is large enough to allow relative movement between the endoscopic instruments. In other procedures, endoscopic instruments are positioned in spaced apart ports. To provide bilateral viewing, a first port and first endoscopic instrument can be positioned on one side of the midsagittal plane of the subject, and the other port and endoscopic instrument can be positioned on the other side of the midsagittal plane. Multiple visualization instruments used in a single procedure can have different viewing characteristics.

The images of the subject's spine can be used to determine implantation information about the interbody fusion implant. Implantation information can include, without limitation, a recommended interbody fusion implant, expansion setting for the interbody fusion implant, and/or recommended implantation position for the interbody fusion implant. The user can be presented information for viewing based on the analysis of the image data, including information for repositioning the interbody fusion implant or information for collapsing the interbody fusion implant. In block 1008, tissue from the intervertebral space can be removed with a tissue removal device positioned at the first entrance. In block 1010, adjacent vertebrae can be distracted using the distraction instrument to enlarge the intervertebral space between the adjacent vertebrae. In block 1012, an interbody spacer, such as an interbody fusion implant, can be delivered to the enlarged intervertebral space. The interbody fusion implant can be delivered in a collapsed configuration through a lumen of the distraction instrument. In block 1014, the interbody fusion implant can be expanded laterally and vertically while a driver instrument is positioned within the distraction instrument positioned at the first entrance and while being endoscopically viewed in block 1016. The lateral and vertical expansion of the interbody fusion implant can be sequential. For example, after the interbody fusion implant is horizontally expanded, the interbody fusion implant can be vertically expanded to provide disc height restoration.

In block 1016, image data can be obtained by an endoscopic instrument. The image data can be video, still images, or other image data. Image data can be obtained before, during, and/or after expansion and analyzed with endoscopic visualization to confirm the position of the expanded interbody fusion implant to improve efficacy of surgeries by allowing the physician to visually assess the procedure. For example, a first image of an implantation site can be obtained by the endoscopic instrument. A second image of the implantation site can be obtained using the endoscopic instrument after delivery of the interbody fusion implant. Image data can be analyzed to determine whether the expanded interbody fusion implant is located at a deployment position based on a position of the expanded interbody fusion implant shown in the second image.

In some embodiments, the first image and the second image can be compared to determine the position of the expanded interbody fusion implant. If the interbody fusion implant is mispositioned, the user can be notified of the mispositioning. The notification can be via an audible alert, visual alert (e.g., an alert displayed on the display 162 at FIG. 1), or by other suitable notification means. In block 1018, the driver instrument can be separated from a locked expanded interbody fusion implant, as discussed in connection with FIG. 10B. The implanted interbody fusion implant can be visualized to confirm proper positioning and deployment of the implant. Visualization can be used if additional procedures are performed. Additional procedures may include, without limitation, delivering bone, growth-promoting materials, or the like to the intervertebral space. Visualization can also be used to view other procedures, such as fixation procedures involving pedicle screws, interspinous spacers, or the like.

The method of FIG. 11 can be performed using various systems disclosed herein. Additional instruments and steps can be performed as needed to provide treatment flexibility. For example, decompression procedures can be performed before or after distracting the adjacent vertebrae at block 1010. Visualization can be used during the decompression procedure to visually identify targeted tissue, as well as ensuring that non-targeted tissue (e.g., nerve tissue) is not traumatized. Although the method is discussed in connection with implanting an interbody fusion implant, the method can be performed to deploy and implant other devices. For example, the method can be used to implant an articulating intervertebral disc. Moreover, the multi-portal systems can be used to implant rigid or fixed interbody fusion devices. The acts and steps in the method of FIG. 11 can be modified based on the features of the implant to perform, for example, an oblique lumbar interbody fusion procedure, a lateral lumbar interbody fusion procedure, a posterior lumbar interbody fusion procedure, a transforaminal lumbar interbody fusion procedure, or an anterior lumbar interbody fusion procedure.

Figure 12:
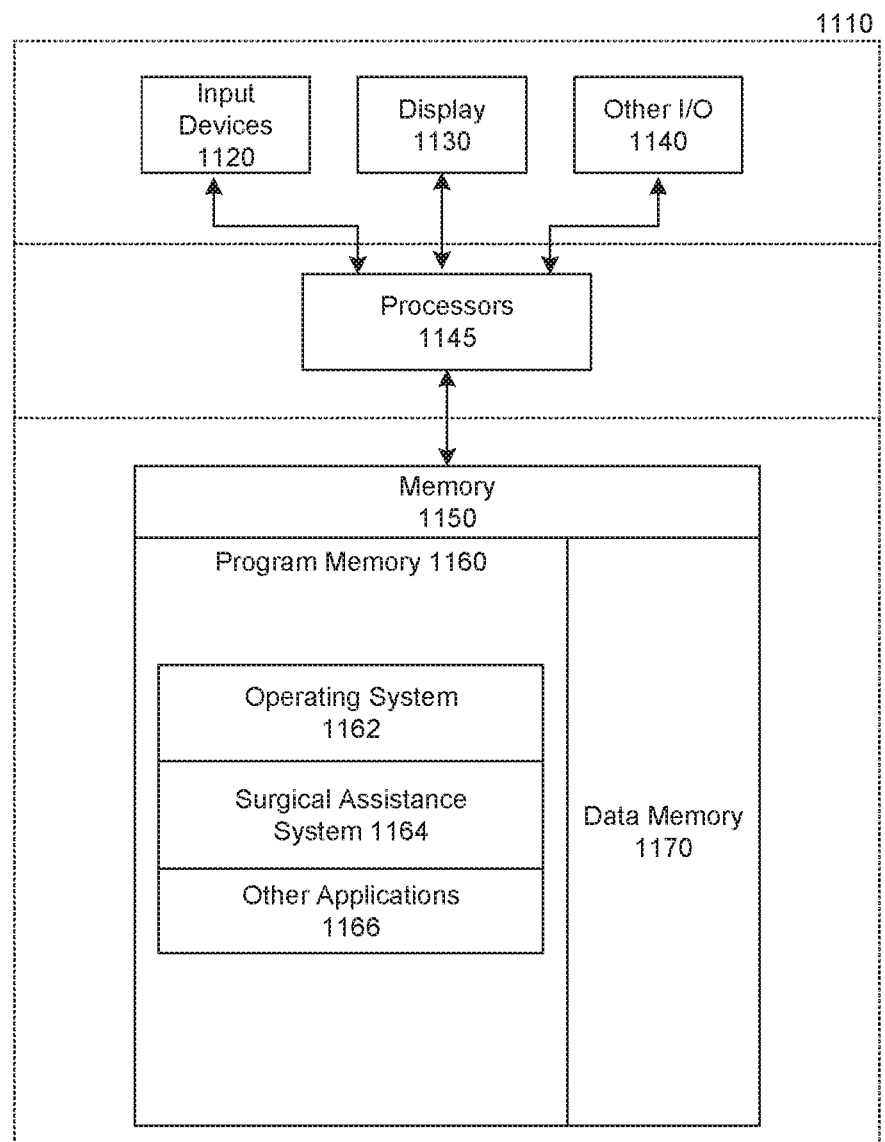
FIG. 12 illustrates a system for providing assistance prior to, during, or after surgery according to an embodiment of the disclosure.

FIG. 12 illustrates a system 1110 for providing surgical assistance according to an embodiment of the disclosure. The system 1110 can improve surgeries by displaying image data, analyzing image data, suggesting steps in a surgical procedure, analyzing implants, or the like. The system 1110 can comprise hardware components that improve surgeries using, for example, a surgical assistance system 1164. In various implementations, the surgical assistance system 1164 can store patient information, obtain image data, analyze information/data to obtain results, and use the results to provide feedback to a user. The surgical assistance system 1164 can analyze still images or video from input devices 1120 to suggested implants for a procedure. For example, the surgical assistance system 1164 can recommend the number, size, and configuration of implants and surgical procedure. Based on the recommendations, the surgical assistance system 1164 can further suggest surgical instruments, a surgical plan, and other information. The surgical plan can include (1) surgical steps, (2) number, size, and/or position of ports, and/or (3) surgical approaches. For example, the surgical assistance system 1164 can annotate an image (e.g., an X-ray image, still image, video, etc.) with suggested insertion points along the subject's skin, surgical procedures (e.g., PLIF, ALIF, LLIF, etc.), access paths, etc. During a procedure, the surgical assistance system 1164 can provide warnings or other feedback to surgeons.

System 1110 can include one or more input devices 1120 that provide input to the processor(s) 1145 (e.g., CPU(s), GPU(s), HPU(s), etc.), notifying it of actions. The actions can be mediated by a hardware controller that interprets the signals received from the input device and communicates the information to the processors 1145 using a communication protocol. The processors 1145 can be used to analyze data, such as image data, to determine whether the expanded interbody fusion implant is located at a deployment position based on a position of the expanded interbody fusion implant shown in an acquired image.

Input devices 1120 can include, for example, visualization devices, such as the visualization device 140 discussed in connection with FIGS. 1-6, endoscopic instruments, imaging devices (e.g., cameras), CRT machines, X-ray machines, or the like. The visualization, in some surgical embodiments, enables surgeons to visually see and verify the vertebral bodies, vertebral spacing, damaged/displaced tissue, intervertebral discs (including bulging portions), presence of unwanted cartilage (e.g., cartilage buildup), bone, or tissue that is causing nerve root compression and damage to normal body functions. This information on the unwanted material can be documented and recorded by saving image data into a computer database and printing color images (e.g., pictures) immediately for reference and recording. The physician can use the information to develop at least a portion of a surgical plan.

Additionally or alternatively, the input devices 1120 can include a mouse, a keyboard, a touchscreen, an infrared sensor, a touchpad, a wearable input device, a camera- or image-based input device, a microphone, or other user input devices. For example, a mouse can be used to select or manipulate image data captured by visualization devices. A keyboard can be used to annotate image data. The number and configuration of the input devices can be selected based on the physician.

Processors 1145 can be a single processing unit or multiple processing units in a device or distributed across multiple devices. Processors 1145 can be coupled to other hardware devices, for example, with the use of a bus, such as a PCI bus or SCSI bus. The processors 1145 can communicate with a hardware controller for devices, such as for a display 1130. The display 1130 can be used to display image data. For example, the display 1130 can correspond to the display 162 in FIG. 1, which can be connected to one or more visualization devices via a wired or wireless connection (FIG. 1 shows a wired connection). The display 1130 can present information for viewing by a user. The presented information can include suggested implant information, suggested surgical instruments, information for implanting devices, information for repositioning the interbody fusion implant, information for collapsing the interbody fusion implant, or the like. The information can be overlaid on or inserted into images or video. In some embodiments, the information can be annotations.

The display 1130 can provide graphical and textual visual feedback to a user. In some implementations, the display 1130 includes the input device as part of the display, such as when the input device is a touchscreen or is equipped with an eye direction monitoring system. In some implementations, the display is separate from the input device. Examples of display devices are: an LCD display screen, a light-emitting diode (LED) display screen, a projected, holographic, or augmented reality display (such as a heads-up display device or a head-mounted device), and so on. The display 1130 can provide high definition visualization.

Other I/O devices 1140 can also be coupled to the processor, such as a network card, video card, audio card, USB, firewire or other external device, camera, printer, speakers, CD-ROM drive, DVD drive, disk drive, or Blu-Ray device. Other I/O devices 1140 can also include input ports for information from directly connected medical equipment such as MRI machines, X-Ray machines, etc. Other I/O devices 1140 can further include input ports for receiving data from these types of machines from other sources, such as across a network or from previously captured data, for example, stored in a database.

The system 1110 can also include a communication device capable of communicating wirelessly or wire-based with a network node. The communication device can communicate with another device or a server through a network using, for example, TCP/IP protocols. The system 1110 can utilize the communication device to distribute operations across multiple network devices.

The processors 1145 can have access to a memory 1150 in a device or distributed across multiple devices. A memory includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 1150 can include program memory 1160 that stores programs and software, such as an operating system 1162, surgical assistance system 1164, and other application programs 1166. Memory 1150 can also include data memory 1170 that can include, for example, implantation site information (e.g., level information, implant deployment information, etc.), surgical plan data, user options or preferences, image data, etc., which can be provided to the program memory 1160 or any element of the system 1110.

Some implementations can be operational with numerous other computing systems, environments, or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium, such as a floppy disc, a hard disk drive, a CD, a DVD, a digital tape, a computer memory, etc.; and a transmission type medium, such as a digital and/or an analog communication medium (e.g., a fiber optic cable, a waveguide, a wired communications link, a wireless communication link, etc.).

C. Surgical Kits

Figure 13:
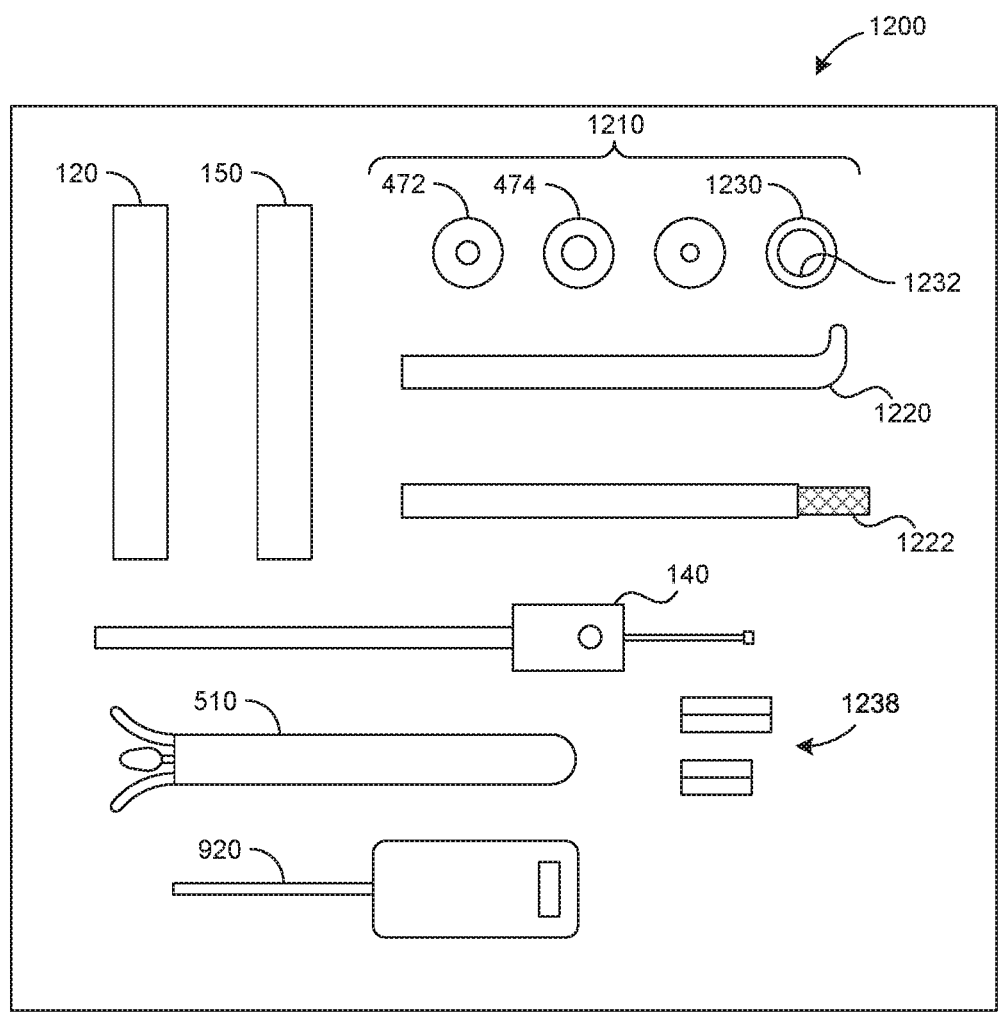
FIG. 13 is a plan view of a surgical kit in accordance with an embodiment of the disclosure.

FIG. 13 is a top plan view of a surgical kit 1200 that includes components discussed in connection with FIGS. 1-11, 14-16, and 18-19. The kit 1200 can include cannulas 120, 150, and a set 1210 of ports. A physician can select appropriate ports based on locations of portal sites and instruments to be utilized. In the illustrative embodiment, the set 1210 includes four ports. A higher or lower number of ports can be provided and can be of the same or different sizes. The kit 1200 can include a connector (e.g., a rigid connector) to couple together cannulas (e.g., cannulas 120, 150, 1400). The cannulas can be coupled together before expanding the interbody fusion device at an intervertebral implantation site.

The kit 1200 can further include a plurality of decompression instruments. In the illustrated embodiment, the kit 1200 includes a debulking instrument 1220 and a reamer 1222. If the decompression instruments are utilized, a physician can select the port 1230 with a large opening 1232. The kit 1200 can also include scalpels, dilators, rongeurs, irrigation cannulas, tissue-detecting or mapping cannulas, expanders, or other surgical instruments. For example, the kit 1200 can include the visualization device 140, the distraction instrument 510, the delivery or deployment instrument 920, and implantable devices 1238. The configuration and components for the kit can be selected based upon the procedure to be performed. Example components for kits are discussed in connection with FIGS. 14-20. A biportal kit with tissue-mapping capabilities can have tissue-detecting cannulas, whereas biportal kits with irrigation functionality can have cannulas with irrigation flowthrough cannulas. Biportal kits can have cannulas configured for both tissue mapping and irrigation. Moreover, one or more of the kit's components can be disposable and can be made, in whole or in part, from metal, polymers, ceramics, composite materials, or other biocompatible and sterilizable materials.

In some embodiments, the kit 1200 is a sterile universal biportal spine surgery kit for performing different procedures. In some biportal procedures, a first port and a second port can be selected from the set 1210 based on the subject's anatomy and procedure to be performed. The first and second ports can be inserted into incisions in the subject. An instrument cannula (e.g., cannula 120, cannula 150, cannula 1400) can be inserted into the first port. Another cannula can be inserted into the second port. Instruments (e.g., debulking instrument 1220, reamer 1222, etc.) positioned in the instrument cannula can be used to perform at least a portion of the procedure while visualization is provided by an imaging device positioned in the imaging cannula.

The surgical instruments can be selected based on the biportal spine procedure to be performed. The instruments can be used to complete one, multiple, or all of steps of the biportal spine procedure with or without utilizing all of the surgical instruments in the kit. Universal spine surgical kits can also have instruments for interbody procedures, decompression procedures, fixation procedures, or combinations thereof. Instruments can be sequentially inserted in the instrument cannula to perform surgical steps. Each of the instruments can be configured to fit within the instrument cannula, thereby allowing the same cannula to be used for the entire procedure. In other procedures, multiple cannulas can be sequentially positioned within the same port. The port can reduce or eliminate tearing of tissue caused by insertion, removal, or positioning of the cannulas.

In some embodiments, a surgery-specific kit 1200 can be configured to perform a particular type of procedure. A physician can select a surgery-specific kit 1200 based on the procedure to be performed.

In some procedures, the location of tissue can be mapped using one or more energy-emitting elements coupled to the instrument cannula and/or the imaging cannula. The energy-emitting elements can be tissue-mapping elements configured to identify tissue beneath the subject's skin. Mapping information can be used to position instruments, imaging devices, cannulas, or the like. Advantageously, mapping can be performed without introducing additional instruments into the subject, thereby reducing procedure complexity, risk of complications, or the like. The tissue of interest can be nerve tissue, connective tissue, anatomical features (e.g., nerve roots, nerve branches, etc.), or the like. For example, mapping can be used to identify the location of nerve roots exiting the vertebral foramen, spinal ganglion, spinal nerves, or the like.

The cannulas can be configured to be fluidically coupled to one or more irrigation apparatuses. The fluidic coupling can be achieved using, without limitation, one or more fittings, connectors, hoses, conduits, or the like. An irrigation apparatus can include one or more fluid control systems, pumps, vacuum or suction devices, conduits, sensors (e.g., flow sensors, fluid pressure sensors, blood sensors, etc.), controllers, or combinations thereof.

The kit 1200 can include one or more expanders that are part of or couplable to a kit component. Expanders can be moved from an unexpanded configuration to an expanded configuration, thereby increasing a working space within the subject. The expander can be a mechanical expander, a pneumatic expander, a self-expanding expander, or the like.

Figure 14:
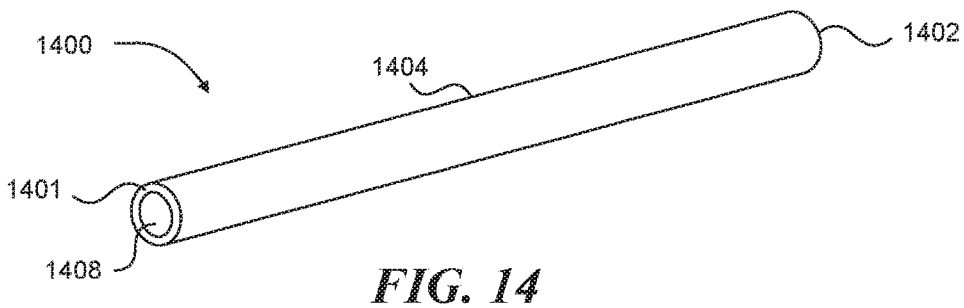
FIG. 14 is a perspective view of a tissue-mapping cannula in accordance with an embodiment of the disclosure.

FIG. 14 is a perspective view of a cannula 1400 in accordance with an embodiment of the disclosure. The cannula 1400 can be used in a manner similar to the cannulas 120, 150, 810, 930 as discussed previously in connection with FIGS. 1, 4-6, 10A, and 13. The cannula 1400 can include a distal end 1401, a proximal end 1402, and an elongated body 1404 having a plurality of lumens extending from the distal end 1401 to the proximal end 1402. The lumens can be used to deliver instruments to a surgical site, deliver fluid into the subject, remove fluid from the subject, or the like. This allows irrigation of the surgical site while instruments can access the site via a working lumen 1408. The working lumen 1408 can be configured to receive a surgical instrument (e.g., a distraction instrument, decompression tool, etc.), a visualization instrument, an implantable device, or other instrument for use during a surgical procedure. The diameter of the working lumen 1408 can be equal to or smaller than about 2 mm, 3 mm, 4 mm, 5 mm, 6 mm, 8 mm, or 10 mm, and the outer diameter of the cannula 1400 can be equal to or smaller than about 3 mm, 4 mm, 5 mm, 6 mm, 8 mm, 10 mm, or 12 mm. Other cannula dimensions can be selected based on the access path, instrument dimensions, and procedure to be performed.

Figure 14A:
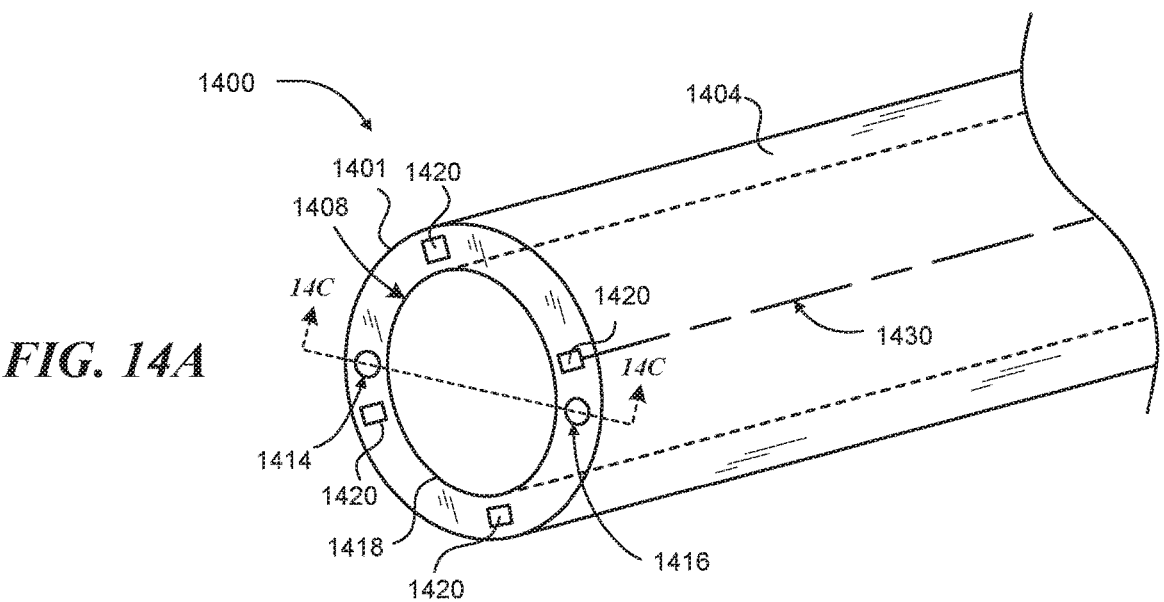
FIG. 14A is a perspective view of a distal end of the cannula of FIG. 14 with lumens and tissue-mapping probes in accordance with an embodiment of the disclosure.
Figure 14B:
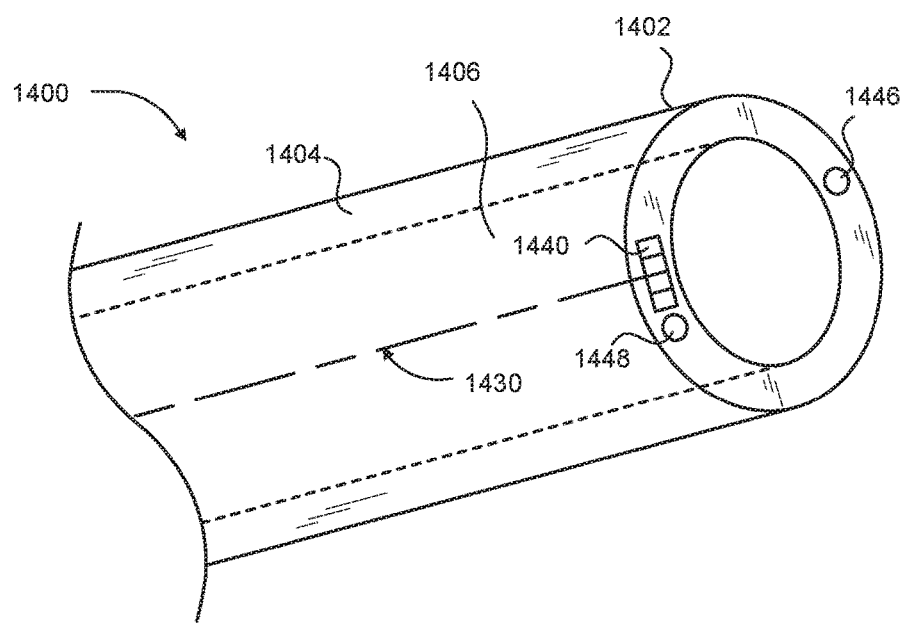
FIG. 14B is a perspective view of a proximal end of the cannula of FIG. 14.
Figure 14C:
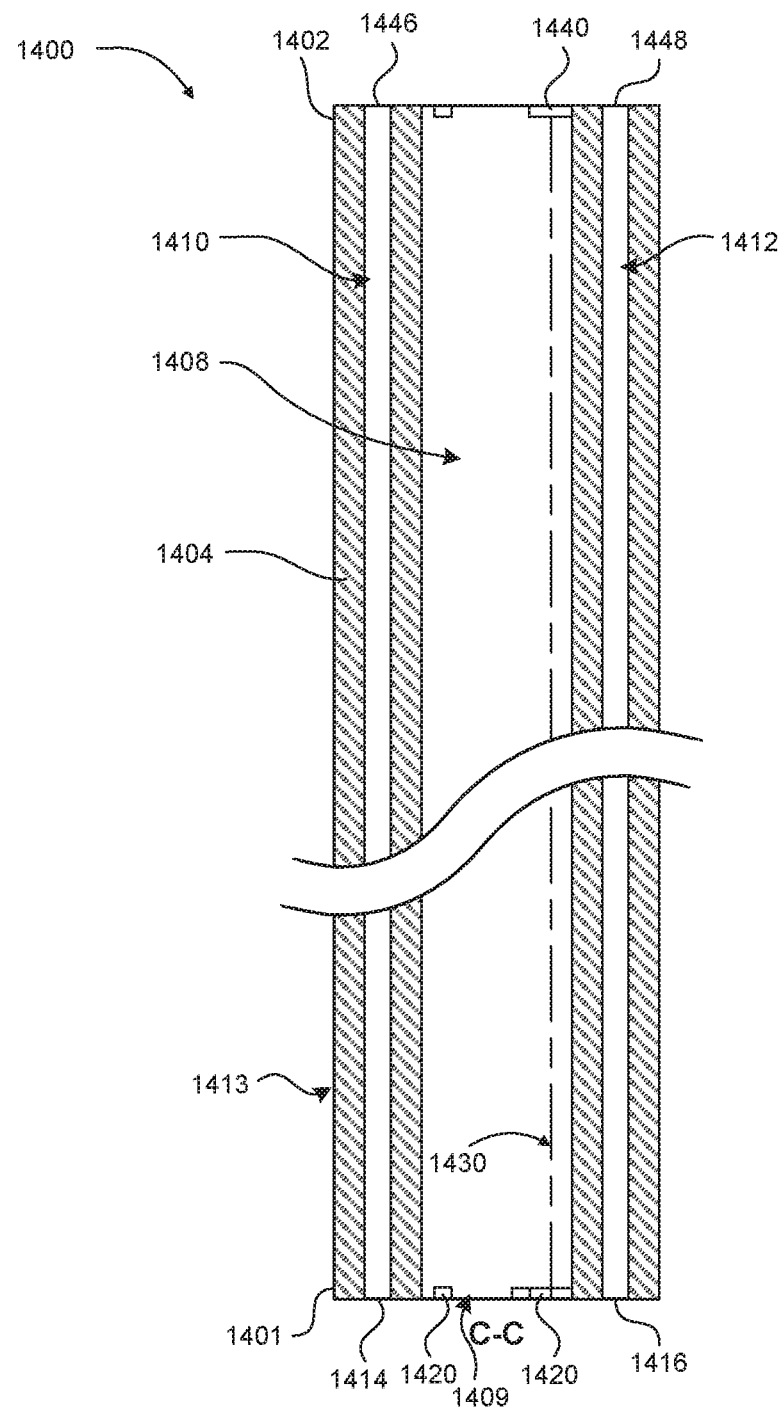
FIG. 14C is a longitudinal cross-sectional view of the cannula of FIG. 14.

FIGS. 14A and 14B are perspective views of the distal end 1401 and the proximal end 1402, respectively, in accordance with an embodiment of the disclosure. FIG. 14C is a longitudinal cross-sectional view as indicated in FIG. 14A. Referring now to FIG. 14A, the distal end 1401 can include a first distal opening 1414, a second distal opening 1416, and a working lumen opening 1418. The first and second openings 1414, 1416 can be positioned on opposite sides of the working lumen opening 1418 and allow fluid flow therethrough. This allows fluid flows to be kept on opposite sides of the working lumen 1408. The configuration, number, and positions of the openings for fluid flow can be selected based on the desired flow of fluid. For example, the number of openings and corresponding lumens can be increased to increase the flow rate of irrigation fluid within the subject.

Referring now to FIG. 14B, the proximal end 1402 can include a first proximal opening 1446 and a second proximal opening 1448. As shown in FIG. 14C, a first fluid lumen 1441 extends between the distal opening 1414 and a proximal opening 1446, and a second fluid lumen 1412 extends between the distal opening 1416 and the proximal opening 1448. The diameter and configurations of the lumens can be selected based on the procedure to be performed. The configurations of the lumens 1408, 1410, 1412 can be, for example, circular, elliptical, or polygonal (including rounded polygonal). In addition, the cross-sectional shapes of lumens can vary along the length of lumens, for example, when a circular lumen terminates at a rectangular aperture at the distal end 1401 of the cannula 1400.

Referring to FIG. 14C, the working lumen 1408 can be substantially centered within the elongate body 1404 so that its distal opening 1409 is correspondingly centered at the face of the distal end 1401, or it can be offset toward the side of the body 1404 depending on its configuration. Similarly, the fluid lumens 1410, 1412 can be positioned within the cannula body 1404 such that their distal apertures 1414, 1416 are located at other positions than those illustrated. For example, the lumens 1410, 1412 could be located adjacent to one another on the same side of the cannula body 1404 to aid in coupling the proximal apertures to a fluid control system. Additionally, according to a variety of embodiments, any of the openings 1406, 1414, 1416, 1446, 1448 can be located along an outer surface 1413 of the cannula body 1404.

With continued reference to FIG. 14C, the fluid lumens 1410, 1412 can be configured to allow surgical irrigation fluid to flow through in either direction according to some embodiments. For example, the first fluid lumen 1410 can be configured to allow a flow of irrigation fluid from a supply connected to the proximal end 1402 to the distal end 1401, while the second fluid lumen 1412 can be configured to allow a flow of irrigation fluid from the distal end 1401 to the proximal end 1402. In various arrangements, both lumens 1410, 1412 can be used to flow fluid in the same direction; only one lumen can be configured to flow fluid, while the other lumen is closed, capped, obturated, or otherwise not used to flow fluid; or neither lumen can be configured to flow fluid and both can be closed, capped, obturated, or otherwise not used to flow fluid.

The cannula 1400 can have one or more tissue-mapping probes. With reference again to FIG. 14A, tissue-mapping probes 1420 can be configured to output energy (e.g., electrical energy, radio frequency energy, electromagnetic energy, ultrasound energy, acoustic energy, etc.) useful for identifying the locations of tissue at a treatment site. The interaction of the energy with various tissue can provide a response that can be measured using a variety of techniques. For example, the tissue-mapping probes 1420 can be neuromonitoring electrodes used with electromyography (EMG) techniques. For example, electrical signals emitted by the electrodes 1420 can depolarize nearby nerves, causing a response in an innervated muscle detectable with an EMG system. Other techniques include, but are not limited to, ultrasonography, fluoroscopy, doppler imaging, and optical imaging. The configuration of the tissue-mapping probes 1420 can be suitable for locating a variety of tissues, including nerve tissue, dura, bone tissue, ligaments, ligamentum flavum, and bone graft material, as well as areas of interest, such as tissue margins, tissue interfaces, or the like.

The arrangement of the tissue-mapping probes 1420 can be selected to aid the tissue-mapping technique. For example, the spaced-apart probes 1420 arranged as illustrated in FIG. 14A can provide directional information. Tissue of interest can respond more strongly to energy output from a probe in closer proximity than from the other probes positioned further away on the cannula. The tissue-mapping probes 1420 can also be configured to emit energy sequentially or in another suitable pattern, such that tissue in each direction associated with a particular tissue-mapping probe can be probed in the same sequence or pattern. This allows tissue-mapping to be performed without adjusting the positions of the tissue-mapping probes 1420. For example, if the distal end 1401 of the cannula 1400 is positioned over a nerve root, the tissue-mapping probes 1420 can be used to detect the presence of a nerve root and additional information, such as the size of a nerve root, orientation of the nerve root, depth of the nerve root, or the like. Advantageously, the mapping can be performed without physically contacting and injuring the nerve tissue. Nerve mapping can be performed to locate spinal nerves around and adjacent to the spinal column.

Referring to FIGS. 14A and 14C, a transmission line 1430 coupled to the tissue-mapping probes 1420 can extend from the distal end 1401 to the proximal end 1402. The transmission line 1430 can include, without limitation, one or more wires, fiber optics, etc., and can be located within a sidewall of the body 1404. The transmission line 1430 can be configured to transmit energy, electrical signals, and/or optical signals, including digital and analog signals of various types. In some embodiments, the transmission line 1430 can be configured to transmit both energy to one tissue-mapping probe and signals received from another tissue-mapping probe. Referring now to FIGS. 14B and 14C, the transmission line 1430 can connect to an interface 1440 at the proximal end 1402. The interface 1440 can include, without limitation, one or more plugs, connectors, or other components that provides a connection point to a tissue-mapping system.

Figure 15:
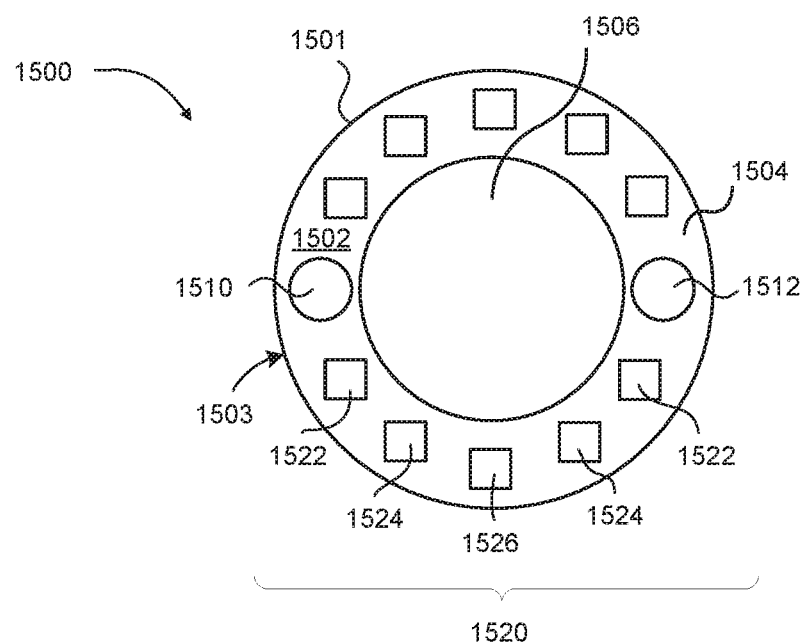
FIG. 15 is an end view of a distal end of a cannula with a plurality of lumens and an array of tissue-mapping probes in accordance with an embodiment of the disclosure.

FIG. 15 is a front elevation view of a cannula 1500. The description of the cannula 1400 of FIGS. 14-14C applies equally to the cannula 1500 unless indicated otherwise. The cannula 1500 can have a tissue-mapping array 1520 with tissue-mapping probes arranged circumferentially around a distal face 1502 of a distal end 1501. The increased number of tissue-mapping probes of FIG. 15 can provide increased directional resolution for tissue-mapping. Additionally, different probes can be configured to emit different types of energy. Other probes can also be configured to receive a return signal.

The tissue-mapping array 1520 can include neuromonitoring electrodes 1522, ultrasonic transducers 1524, and photoacoustic sensors 1526. The arrangement of multiple modalities of tissue-mapping can improve tissue location and visualization. Neuromonitoring electrodes 1522 can aid the positioning of the cannula so as to avoid nerve contact during insertion, while ultrasonic emitters and photoacoustic sensors can provide information related to the location of various tissues and tissue interfaces. The number (e.g., five, six, eight, ten, etc.), positions, and configuration of the tissue-mapping probes can be selected based on the mapping to be performed. For example, the number of electrodes can be increased to provide higher-resolution mapping. In some embodiments, some probes can be arrayed around the side of the distal end, while others are arrayed on the distal face 1502. The probes can be flush with the outer surface 1503 of the cannula body or slightly recessed within the cannula body. In other embodiments, a probe can extend past the surface 1503.

Figure 16:
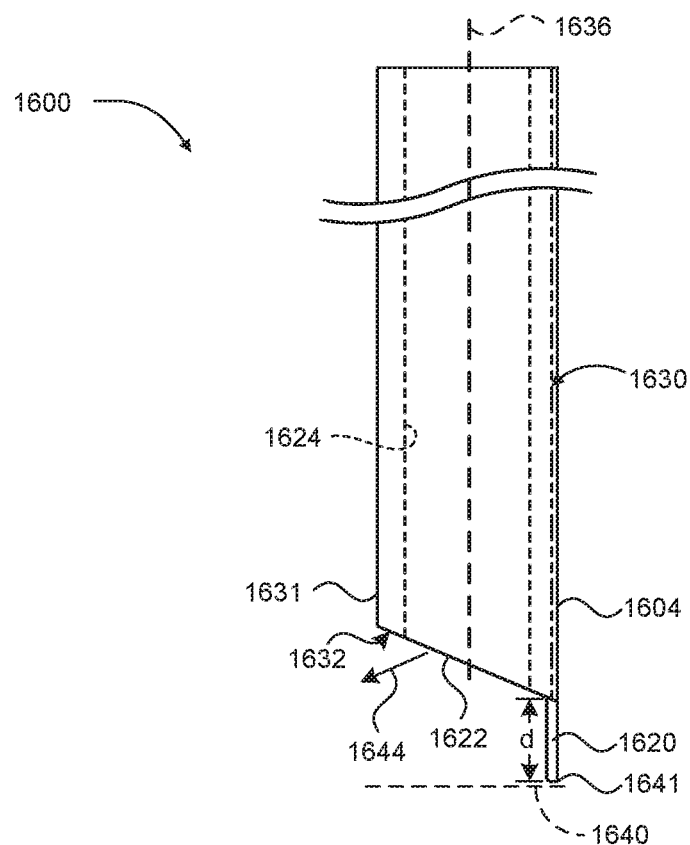
FIG. 16 is a side view of a cannula with a protruding tissue-mapping probe according to an embodiment of the disclosure.

FIG. 16 is a side view of a cannula including a tissue-mapping probe 1620 according to a particular embodiment of the disclosure. The description of the cannula 1400 of FIGS. 14-14C and cannula 1500 of FIG. 15 applies equally to the cannula 1600 unless indicated otherwise. The tissue-mapping probe 1620 extends distally from the distal end 1631 of the cannula body 1604. The distance d of the tissue-mapping probe 1620 extends from the body 1640 can be selected based on the desired clearance for the lumen opening 1622 of the working lumen 1624 (shown in dashed line). Such probe protrusion can aid in techniques like EMG during the guided insertion of a cannula, where the probe leads the body of the cannula and can determine tissue location before the tissue is contacted by the cannula. In some embodiments, the distal end 1631 can have a distal face 1632 that is generally angled with respect to a longitudinal axis 1636 of the cannula 1600. For example, the illustrated face 1632 can be non-orthogonal with respect to the longitudinal axis 1636 to provide lateral clearance to instruments. When the probe 1620 is adjacent or contacting tissue 1640 (illustrated in dashed line), instruments can be easily passed out to the working lumen in a lateral direction, as indicated by the arrow 1644. Advantageously, the probe 1620 can physically contact the tissue to help maintain spacing between the tissue 1640 and the working instrument. The configuration and position of the probe 1620 can be selected based on the desired mapping and tissue interaction. For example, the probe 1620 can have a blunt or rounded tip 1641 configured to slide atraumatically across tissue. In other embodiments, the tip 1641 can be pointed or relatively sharp to pierce tissue. In some procedures, the piercing probe 1620 can be inserted into tissue to map tissue underlying the exposed tissue surface.

Figure 17:
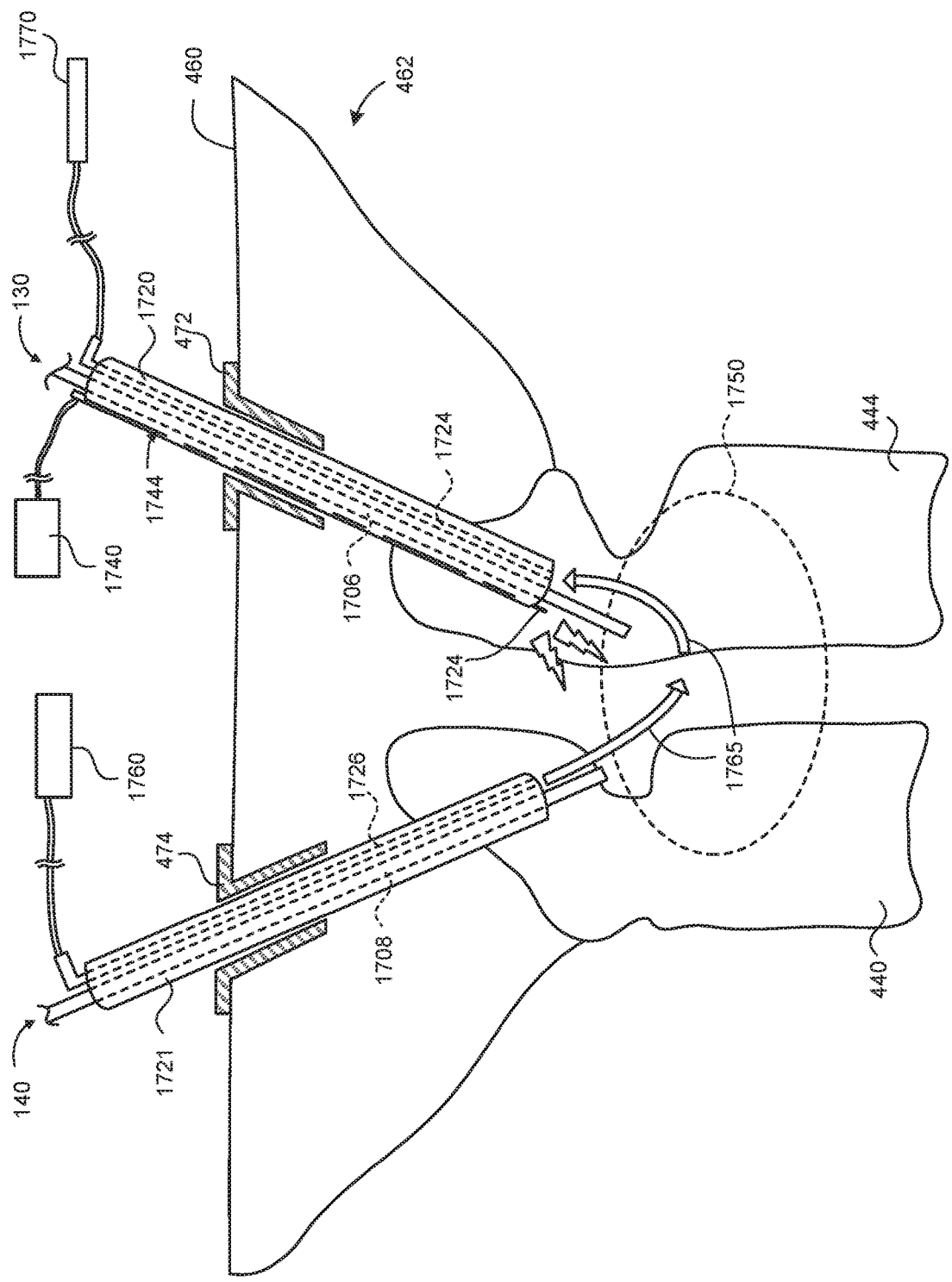
FIG. 17 is a side view of a surgical system with cannulas that circulate surgical irrigation fluid and map tissue in accordance with an embodiment of the disclosure.

FIG. 17 is a detailed side view of cannulas 1720, 1721 positioned to perform a procedure in accordance with embodiments of the disclosure. Cannulas 1720, 1721 can be positioned in respective ports 472, 474 and extend through the subject's skin 460 and through subcutaneous tissue 462. The cannulas 1720, 1721 can be inserted through the respective ports 472, 474 such that their distal ends are adjacent to or at a treatment site 1750 (generally identified in dashed line). The insertion can be guided by a tissue-mapping probe 1724 that is operably coupled to a tissue-mapping system 1740 via a transmission line 1744. The cannula 1720 can have the features of the cannula 1600 discussed in connection with FIG. 16.

The cannulas 1720, 1721 have fluid lumens 1725, 1726, respectively, configured to circulate surgical irrigation fluid through the treatment site 1750. The fluid lumen 1726 can be fluidically connected to a fluid supply system 1760. The fluid lumen 1725 can be fluidically connected to a fluid return system 1770 at the proximal end of the cannula 1720. In some embodiments, the fluid supply system 1760 and fluid return system 1770 are elements of an integrated fluid control system. The systems 1760, 1770 can include components and features discussed in connection with system 1110.

The circulating fluid flow can be controlled and monitored by the fluid supply system 1760 and/or the fluid return system 1770. The flow can be present while an instrument assembly 130 and visualization instrument 140 are positioned within the working lumens 1706, 1708 of the cannulas 1720, 1722, respectively. The irrigation fluid can improve visibility at the treatment site 1750 and provide improved control of fluid pressure and flow rate during a procedure. In various embodiments, the cannulas 1720, 1722 can be configured as described with regard to cannulas 1400, 1500, and 1600 discussed above in connection with FIGS. 14A-C, 15, and 16, and as described below with regard to cannula 1800.

The tissue-mapping probe 1724 can be used to map tissue near the treatment site 1750 while the instrument assembly 130 and visualization instrument 140 are positioned within the cannulas 1720, 1722, respectively. In this way, according to some embodiments, a physician can receive periodic or continual updates regarding the position of tissue near or at the treatment site 1750 as the surgical procedure progresses.

The tissue-mapping system 1740 can be an element of the system 1110 for providing surgical assistance as discussed above in connection with FIG. 12. The tissue-mapping system 1740 can include, without limitation, one or more displays, computers, computing devices, processors, displays, or combinations thereof. Information relating to the location of tissue (e.g., tissue location information determined by energy output by tissue-mapping probe 1724), and/or information relating to the visualization of the treatment site 1750 (e.g., visualization information obtained via the visualization instrument 140) can be processed and combined and presented to the physician to improve surgeries. In some embodiments, the tissue-mapping system 1740 can provide a visualization of tissue locations at the treatment site 1750 and overlay this visualization onto image data (e.g., still images, video, etc.) obtained from the visualization instrument. The procedure of FIG. 17 can employ other cannulas, ports, or components discussed herein.

Figure 18:
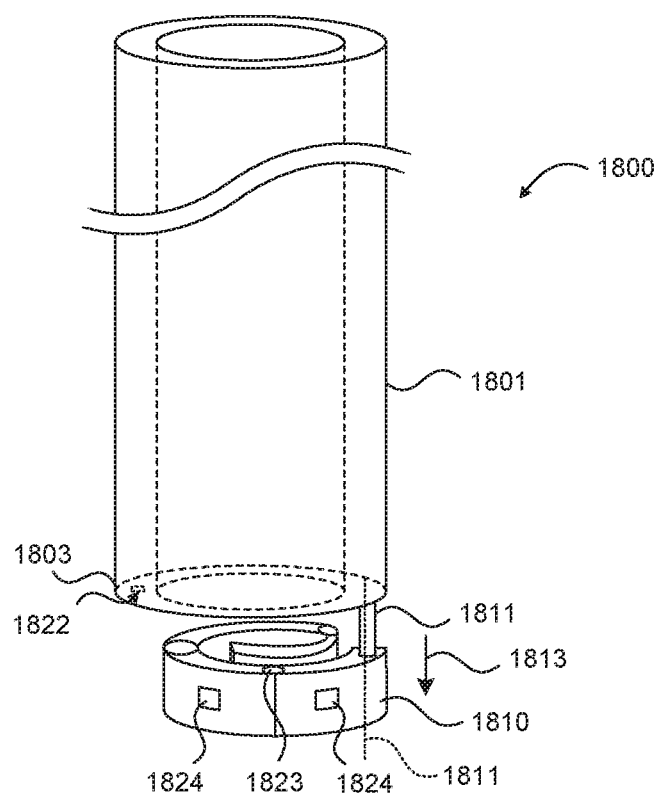
FIG. 18 is a side view of a cannula with a deployable expander carrying tissue-mapping probes in accordance with an embodiment of the disclosure.
Figure 19:
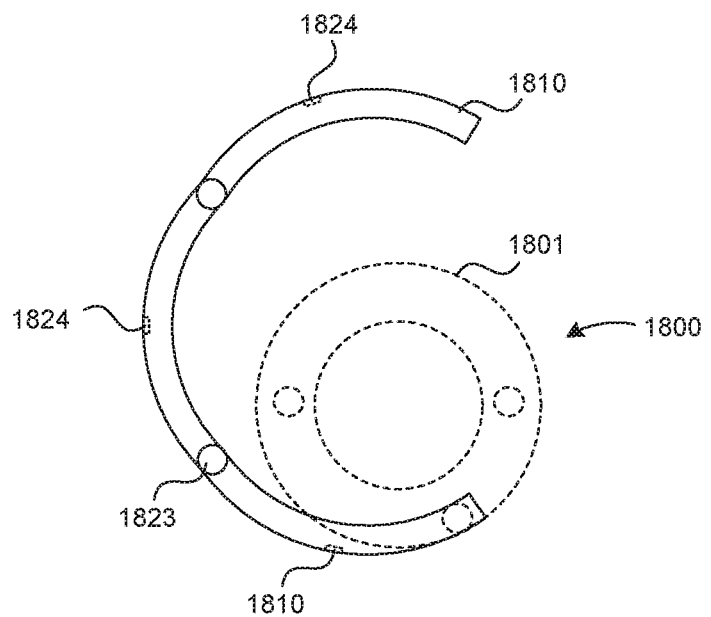
FIG. 19 is an enlarged top view of the cannula of FIG. 18 with the expander in a deployed configuration.

FIG. 18 is a side view of a cannula 1800 according to embodiments of the disclosure. FIG. 19 is a top view of the cannula 1800 with the cannula body 1801 shown in dashed line. The cannula 1800 can include an expander or spacer 1810 ("expander 1810") coupled to a distal end 1803 of an elongate body 1801 of the cannula 1800. The expander 1810 can have a stowed configuration (as illustrated in FIG. 18) and a deployed configuration (as illustrated in FIG. 19). The expander 1810 can be translated relative to the distal end 1803 (FIG. 18) via a movable coupler 1811. The movable coupler 1811 can be moved away from the distal end 1803, as indicated by arrow 1813 of FIG. 18. In some procedures, the coupler 1811 is slidably disposed within a side wall of the elongate body 1801 such that a physician can manually push the expander 1810 distally. In other embodiments, the coupler 1811 is fixedly coupled to elongate body 1801. For example, the coupler 1811 can be a rod integrally formed with or coupled to the elongate body 1801. In further embodiments, the coupler 1811 can be rotatably coupled to the distal end 1803. This allows the spacer 1810 to be rotated relative to elongate body 1801. For example, the expander 1810 can be rotated about a longitudinal axis 1811 of the coupler 1811. The configuration of the coupling arrangement can be selected based on the desired movability of the expander 1810.

The expander 1810 can have an articulatable body movable between a ring-shaped or spiral configuration and expanded configuration. FIG. 18 shows the expander 1810 in a spiral configuration. Articulated segments can be connected via joints or pivots to move toward the expanded configuration of FIG. 19. The segmented sections of the body of the expander 1810 can be connected by joints 1823 (one identified in FIG. 19) that can include, without limitation, one or more hinges, joints, living hinges, or the like. The expander 1810 can include tissue-mapping elements, contact sensors, anchors, or other features for engaging or contacting tissue. In some embodiments, the expander 1810 can include one or more deployable arms or tines to allow further expansion of the spacer 1810. When deployed, the expander can create a working volume at a treatment site within a subject.

In other embodiments, the expander can be an expandable cone, funnel, or other suitable shape to provide increased working volume near or at a treatment site. The expander allows visualization of the volume partially bounded by the expander when in the deployed configuration. For example, a visualization instrument positioned within a second cannula near to the cannula 1800 can visualize the region interior to the spacer by viewing through an unenclosed side of the expander 1810. In some embodiments, the expander 1810 can have an aperture, a window, or other opening to permit visualization of the partially bounded region.

The expander 1810 can have tissue-mapping probes 1824 positioned at the exterior surface of the segments. The tissue-mapping probes 1824 can be configured to output energy similarly to the tissue-mapping probes 1420, 1520, 1620 discussed above in connection with FIGS. 14A-16. The tissue-mapping probes 1824 can be in addition to tissue-mapping probe 1822 (FIG. 18) positioned at the distal end of the cannula 1800. The tissue-mapping probes 1824 can aid in the deployment of the expander 1810, help locate and orient the expander 1810, and provide feedback to avoid contacting nerve tissue or other tissue.

Figure 20:
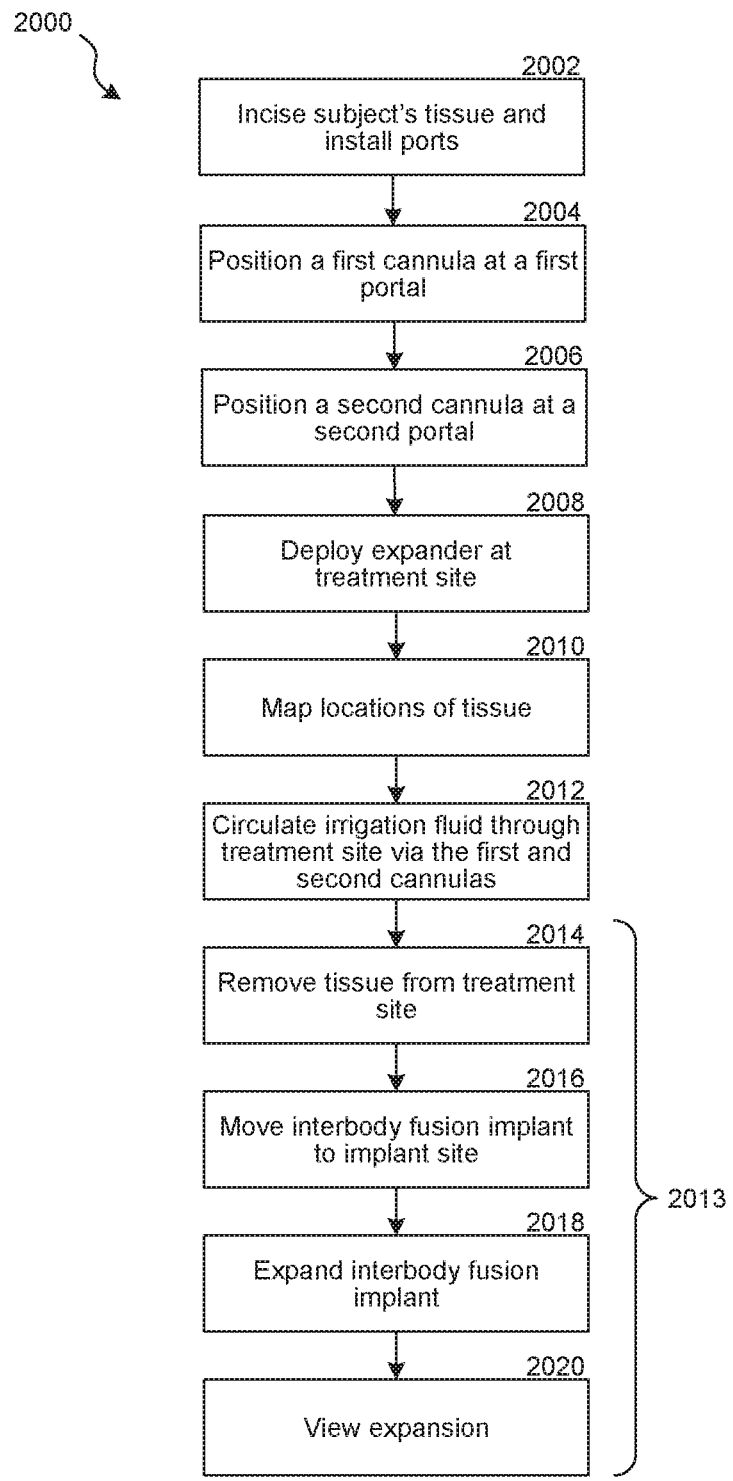
FIG. 20 is a flow diagram illustrating a method for performing multi-portal spine surgery with circulated irrigation flow and/or tissue-mapping in accordance with an embodiment of the disclosure.

FIG. 20 is a flow diagram illustrating a method 2000 for treating a subject in accordance with an embodiment of the disclosure. At block 2002, a subject's tissue is incised and incisions at locations in the incisions. Block 2002 can be similar to block 1002 described above in connection with FIG. 11. At block 2004, a first cannula can be positioned in a port at a first location in the subject's tissue. An instrument, for example, a distraction instrument, can be inserted through the working lumen of the cannula. Utilization of distraction instruments and cannulas are discussed in connection with FIGS. 5-8. Various additional embodiments of cannulas are discussed in connection with FIGS. 14A-16 and 18-19.

At block 2006, a visualization device can be inserted through a second cannula positioned at a second portal site. Utilization of a visualization device at a second portal site is discussed above in connection with FIG. 11, for embodiments where a visualization device may be used with a second cannula at a second portal site.

In optional block 2008, a spacer can be deployed at a treatment site. The expander can enlarge a working volume at the treatment site to improve irrigation fluid flow, improve visualization, and/or aid in tissue-mapping. For example, the expander can increase visibility and/or access to the surgical location and can be configured to maintain an expanded configuration. The expander can be engageable and disengageable with the cannula body. Deploying an expander is discussed above in connection with FIGS. 18 and 19.

At block 2010, tissue-mapping probes on the first and/or second cannulas can be used to determine the locations of tissue at or near a treatment site within the subject. Tissue-mapping probes and tissue-mapping systems are discussed above in connection with FIGS. 14A-19. In some embodiments, the tissue-mapping system can provide information in addition to image data provided by an endoscopic instrument. The information can be combined with the visualization image data to provide an image overlay or other indication of the location of tissue within the subject. The tissue-mapping information can be used if additional procedures are performed.

In block 2012, irrigation fluid can be circulated through a treatment site via the first and second cannulas. The fluid lumen of the first cannula can be fluidically connected to a fluid supply system to supply fluid at a controlled pressure or flow rate. The fluid lumen of the second cannula can be fluidically connected to a fluid return system to return fluid from the treatment site. The deployed expander can aid in controlling the fluid flow by providing a controlled boundary for the working volume at the treatment site. According to several embodiments, the first and second cannulas can have additional fluid lumens that can be connected to a fluid control system. The fluid control system can then be used to configure a fluid lumen to supply or return irrigation fluid.

Thus, a first cannula can have, for example, both a fluid lumen configured to supply irrigation fluid and a fluid lumen configured to return irrigation fluid, while a second cannula has a fluid lumen configured to return irrigation fluid and a fluid lumen configured to neither supply nor return irrigation fluid.

At procedure 2013, blocks 2014-2020 describe various steps, including removing tissue from a treatment site, moving an interbody fusion implant to an implant site, expanding the implant, and visualizing the expansion. These steps are similar to steps at blocks 1008-1016 discussed above in connection with FIG. 11. Steps can be removed and performed in different orders.

The components discussed herein can be mixed and matched to provide desired functionality. For example, the cannulas and instruments discussed in connection with FIGS. 1 and 13 can include tissue expanders, tissue-mapping elements, visualization devices, or other features to provide desired functionality. The components can be integrated into instruments and cannulas or can be separate components. For example, the expander 1810 discussed in connection with FIGS. 18 and 19 can be coupled to other cannulas discussed herein using a clamp, pin connectors, or other suitable connection arrangement. This allows the expander 1810 to be coupled to a wide variety of different types of cannulas. Additionally, distal regions of instruments, cannulas, and expanders can have atraumatic designs to reduce or limit tissue injury. By way of example, the expander 1810 of FIGS. 18 and 19 can have rounded distal regions to help slide along tissue, thereby limiting or preventing tissue injury. In other embodiments, expanders and cannulas can have relatively sharp edges to facilitate cutting, abrading, or otherwise manipulating tissue. A kit can have both atraumatic and non-atraumatic instruments to allow a user to select how tissue may or may not be affected by the instruments and cannulas. Although lumens are within cannulas, a separate tube can be couplable to cannulas. For example, a bone dust removal tube can include a connector or clamp for detachably coupling to cannulas.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Features from various systems, methods, and instruments can be combined with features disclosed in U.S. Pat. Nos. 8,632,594, 9,308,099, 10,105,238 and 10,201,431, which are hereby incorporated by reference and made a part of this application. Variations of the implants are contemplated. For example, the interbody spacer 910 (FIGS. 9A-9C) may be provided with different overall heights covering a range of intervertebral disc heights. In other examples, the interbody spacer 910 may be provided with different lordotic and/or kyphotic angles. In still other examples, the interbody spacer 910 may be provided with other patterns or features, such as spikes, protrusions, or the like, on the bone contacting surfaces that provide stability and/or resistance to shifting positions. The implant may be made from metal, polymers, ceramic, composite, or other biocompatible and sterilizable material. Different materials may be combined in what is described herein as a single part. A surgical kit can include components discussed in connection with, for example, FIGS. 1-11, 14-16, and 18-19. The kit can include cannulas, ports, fluid components, tissue-mapping elements, expanders, combinations thereof, or the like.

Systems, components, and instruments disclosed herein can be disposable or reusable. For example, the ports, instruments, or cannulas can be disposable to prevent cross-contamination. As used herein, the term "disposable" when applied to a system or component (or combination of components), such as an instrument, a tool, or a distal tip or a head, is a broad term and generally means, without limitation, that the system or component in question is used a finite number of times and is then discarded. Some disposable components are used only once and are then discarded. In other embodiments, the components and instruments are non-disposable and can be used any number of times. In some kits, all of the components can be disposable to prevent cross-contamination. In some other kits, components (e.g., all or some of the components) can be reusable.

Where the context permits, singular or plural terms may also include the plural or singular term, respectively. Moreover, unless the word 'or' is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

What is claimed is:

1. A cannula comprising:
   an elongate body including a proximal end and a distal end;
   a plurality of lumens extending from the proximal end to the distal end of the elongate body, wherein the plurality of lumens includes a first fluid lumen configured to provide flow of fluid therethrough and a working lumen configured for allowing a surgical instrument to pass therethrough; and
   a plurality of tissue-mapping probes disposed at the distal end of the elongate body and spaced circumferentially around the working lumen, wherein the tissue-mapping probes each include an electrode configured to emit energy to detect tissue such that the plurality of tissue-mapping probes acquire additional information of the detected tissue.

2. The cannula of claim 1, further comprising at least one transmission line within the elongate body and electrically coupled to the plurality of tissue-mapping probes, and wherein the plurality of tissue-mapping probes are configured to emit the energy for identifying nerve tissue while the surgical instrument is positioned in the working lumen.

3. The cannula of claim 1, wherein the plurality of lumens further includes a second fluid lumen configured to provide flow of fluid therethrough.

4. The cannula of claim 3, wherein:
   the first fluid lumen is configured to provide flow of irrigation fluid from the proximal end to the distal end and into a surgical site; and
   the second fluid lumen is configured to provide flow of irrigation fluid from the surgical site through the distal end and to the proximal end.

5. The cannula of claim 4, wherein the proximal end of the cannula is configured to be coupled to a surgical irrigation supply system to fluidically couple one or both of the first fluid lumen and the second fluid lumen to the surgical irrigation supply system.

6. The cannula of claim 1, wherein the plurality of tissue-mapping probes include neuromonitoring electrodes.

7. The cannula of claim 1, wherein the plurality of tissue-mapping probes are operably coupled to at least one transmission line extending along the elongate body.

8. The cannula of claim 7, wherein the at least one transmission line is operably connectable to a tissue-mapping system programmed to identify tissue based, at least in part, on output from the plurality of tissue-mapping probes.

9. The cannula of claim 8, wherein the at least one transmission line is configured to transmit one or both of electrical signals and optical signals.

10. The cannula of claim 1 wherein the additional information includes at least one of a nerve root size, a nerve root orientation, or a nerve root depth.

11. A kit for multi-portal spine surgery techniques, the kit comprising:
    a plurality of cannulas each including a working lumen, a first fluid lumen, a second fluid lumen, and at least one probe, wherein at least one of the plurality of cannulas includes a plurality of tissue-mapping probes disposed at the distal end thereof and spaced circumferentially around the working lumen, wherein the tissue-mapping probes each include an electrode configured to emit energy to detect tissue such that the plurality of tissue-mapping probes acquire additional information of the detected tissue; and
    a plurality of surgical ports each sized to receive at least one of the plurality of cannulas therethrough.

12. The kit of claim 11, wherein the surgical ports are configured to extend through a subject's skin and fascia.

13. The kit of claim 11, wherein the kit is a sterile universal spine surgery kit.

14. The kit of claim 11, further comprising:
    at least one surgical instrument; and
    packaging holding the plurality of cannulas, the plurality of ports, and at least one surgical instrument.

15. The kit of claim 14, wherein the at least one surgical instrument includes one or more of a distraction instrument, a delivery instrument, a scalpel, a dilator, a rongeur, a debulking instrument, and a reamer.

16. The kit of claim 11, further comprising at least one implantable device.

17. The kit of claim 11, further comprising a visualization instrument.

* * * * *